United States Patent
Pavlovic et al.

(10) Patent No.: US 12,332,902 B2
(45) Date of Patent: Jun. 17, 2025

(54) FILTERING INDIVIDUAL DATASETS IN A DATABASE

(71) Applicant: Ancestry.com DNA, LLC, Lehi, UT (US)

(72) Inventors: Milos Pavlovic, Sandy, UT (US); Ross Eugene Curtis, Cedar Hills, UT (US)

(73) Assignee: Ancestry.com DNA, LLC, Lehi, UT (US)

( * ) Notice: Subject to any disclaimer, the term of this patent is extended or adjusted under 35 U.S.C. 154(b) by 181 days.

(21) Appl. No.: 18/137,232

(22) Filed: Apr. 20, 2023

(65) Prior Publication Data
US 2023/0342364 A1 Oct. 26, 2023

Related U.S. Application Data

(60) Provisional application No. 63/332,811, filed on Apr. 20, 2022.

(51) Int. Cl.
*G06F 16/24* (2019.01)
*G06F 16/2457* (2019.01)
(Continued)

(52) U.S. Cl.
CPC ....... *G06F 16/2457* (2019.01); *G06N 3/0464* (2023.01); *G06N 3/08* (2013.01)

(58) Field of Classification Search
CPC ..... G06F 16/2457; G06N 3/0464; G06N 3/08
See application file for complete search history.

(56) References Cited

U.S. PATENT DOCUMENTS

D169,994 S 7/1953 Soffer et al.
D175,257 S 8/1955 Hopkins
(Continued)

FOREIGN PATENT DOCUMENTS

EP 2370929 A1 10/2011
EP 3276526 A1 1/2018
(Continued)

OTHER PUBLICATIONS

Glodzik, D. et al. "Inference of Identity by Descent in Population Isolates and Optimal Sequencing Studies." European Journal of Human Genetics, vol. 21, Jan. 30, 2013, pp. 1140-1145.
Gusev, A. et al. "Whole Population, Genome-Wide Mapping of Hidden Relatedness." Genome Research, vol. 19, No. 2, Oct. 29, 2008, pp. 318-326.
Huff, C. D. et al. "Maximum-Likelihood Estimation of Recent Shared Ancestry (ERSA)." Genome Research, vol. 21, Feb. 8, 2011, pp. 768-774.
(Continued)

*Primary Examiner* — Merilyn P Nguyen
(74) *Attorney, Agent, or Firm* — Fenwick & West LLP

(57) ABSTRACT

A user of a genetic database may create and build upon their family tree in the database. For new users, creating a family tree can be difficult and time consuming. Even for users with established family trees, extending their family tree is a challenge requiring extensive research. Disclosed herein are embodiments for assisting users of a genetic database with building their family trees. In some embodiments, a method for assisting with constructing family trees includes receiving a target individual's genetic dataset. The method identifies a plurality of matched individuals who genetically match the target individual. The method identifies potential ancestors who are potential common ancestors between the target individual and one of the matched individuals. The method inputs a set of features related to the target individual to a machine learning model and filters the potential common ancestors to determine a subset of likely common ancestors for the target individual.

18 Claims, 21 Drawing Sheets

(51) Int. Cl.
*G06N 3/0464* (2023.01)
*G06N 3/08* (2023.01)

(56) References Cited

U.S. PATENT DOCUMENTS

| | | |
|---|---|---|
| 2,793,776 A | 5/1957 | Lipari |
| D196,112 S | 8/1963 | Esser |
| 3,831,742 A | 8/1974 | Gardella et al. |
| 4,131,016 A | 12/1978 | Layton |
| 4,184,483 A | 1/1980 | Greenspan |
| 4,217,798 A | 8/1980 | McCarthy et al. |
| 4,301,812 A | 11/1981 | Layton et al. |
| 4,312,950 A | 1/1982 | Snyder et al. |
| D277,736 S | 2/1985 | Long |
| D286,546 S | 11/1986 | Funahashi |
| 4,935,342 A | 6/1990 | Seligson et al. |
| 4,982,553 A | 1/1991 | Itoh |
| D330,011 S | 10/1992 | Miller et al. |
| 5,283,038 A | 2/1994 | Seymour |
| 5,393,496 A | 2/1995 | Seymour |
| 5,396,986 A | 3/1995 | Fountain et al. |
| D362,623 S | 9/1995 | Ma |
| 5,714,341 A | 2/1998 | Thieme et al. |
| D392,187 S | 3/1998 | King |
| 5,736,322 A | 4/1998 | Goldstein |
| 5,736,355 A | 4/1998 | Dyke et al. |
| 5,830,154 A | 11/1998 | Goldstein et al. |
| 5,830,410 A | 11/1998 | Thieme et al. |
| D412,107 S | 7/1999 | Bosshardt |
| 5,927,549 A | 7/1999 | Wood |
| 5,933,498 A | 8/1999 | Schneck et al. |
| 6,003,728 A | 12/1999 | Elliott |
| 6,048,091 A | 4/2000 | McIntyre et al. |
| 6,152,296 A | 11/2000 | Shih |
| D437,786 S | 2/2001 | van Swieten et al. |
| 6,228,323 B1 | 5/2001 | Asgharian et al. |
| 6,362,473 B1 | 3/2002 | Germanus |
| 6,428,962 B1 | 8/2002 | Naegele |
| 6,458,546 B1 | 10/2002 | Baker |
| D470,240 S | 2/2003 | Niedbala et al. |
| D471,234 S | 3/2003 | Okutani |
| 6,543,612 B2 | 4/2003 | Lee et al. |
| 6,548,256 B2 | 4/2003 | Lienau et al. |
| D474,280 S | 5/2003 | Niedbala et al. |
| 6,627,152 B1 | 9/2003 | Wong |
| 6,760,731 B2 | 7/2004 | Huff |
| 6,786,330 B2 | 9/2004 | Mollstam et al. |
| D507,351 S | 7/2005 | Birnboim |
| 6,939,672 B2 | 9/2005 | Lentrichia et al. |
| 6,992,182 B1 | 1/2006 | Müller et al. |
| D515,435 S | 2/2006 | Muehlhausen |
| 7,055,685 B1 | 6/2006 | Patterson et al. |
| D537,416 S | 2/2007 | Fortin et al. |
| 7,178,683 B2 | 2/2007 | Birkmayer et al. |
| 7,214,484 B2 | 5/2007 | Weber et al. |
| 7,297,485 B2 | 11/2007 | Bornarth et al. |
| 7,303,876 B2 | 12/2007 | Greenfield et al. |
| D573,465 S | 7/2008 | Kogure et al. |
| D574,507 S | 8/2008 | Muir et al. |
| D584,357 S | 1/2009 | Oka |
| 7,482,116 B2 | 1/2009 | Birnboim |
| D586,856 S | 2/2009 | Yagyu |
| 7,537,132 B2 | 5/2009 | Marple et al. |
| 7,544,468 B2 | 6/2009 | Goldstein et al. |
| 7,589,184 B2 | 9/2009 | Hogan et al. |
| 7,645,424 B2 | 1/2010 | O'Donovan |
| D612,730 S | 3/2010 | Rushe |
| 7,748,550 B2 | 7/2010 | Cho |
| 7,854,104 B2 | 12/2010 | Cronin et al. |
| 7,858,396 B2 | 12/2010 | Corstjens et al. |
| D631,350 S | 1/2011 | Beach et al. |
| D631,553 S | 1/2011 | Niedbala et al. |
| D640,794 S | 6/2011 | Sunstrum et al. |
| D640,795 S | 6/2011 | Jackson et al. |
| 7,998,757 B2 | 8/2011 | Darrigrand et al. |
| 8,038,668 B2 | 10/2011 | Scott et al. |
| 8,062,908 B2 | 11/2011 | Mink et al. |
| 8,158,357 B2 | 4/2012 | Birnboim et al. |
| 8,221,381 B2 | 7/2012 | Muir et al. |
| D673,265 S | 12/2012 | Nonnemacher et al. |
| 8,425,864 B2 | 4/2013 | Haywood et al. |
| 8,431,384 B2 | 4/2013 | Hogan et al. |
| 8,463,554 B2 | 6/2013 | Hon et al. |
| 8,470,536 B2 | 6/2013 | Birnboim et al. |
| D693,682 S | 11/2013 | Bahri et al. |
| 8,673,239 B2 | 3/2014 | Niedbala et al. |
| 8,728,414 B2 | 5/2014 | Beach et al. |
| 8,855,935 B2 | 10/2014 | Myres et al. |
| D718,127 S | 11/2014 | Moriyama et al. |
| 9,040,675 B2 | 5/2015 | Bales et al. |
| 9,072,499 B2 | 7/2015 | Birnboim et al. |
| 9,079,181 B2 | 7/2015 | Curry et al. |
| D743,044 S | 11/2015 | Jackson et al. |
| D743,571 S | 11/2015 | Jackson et al. |
| 9,207,164 B2 | 12/2015 | Muir et al. |
| D757,546 S | 5/2016 | Seifer |
| 9,390,225 B2 | 7/2016 | Barber et al. |
| 9,410,147 B2 | 8/2016 | Gundling |
| 9,416,356 B2 | 8/2016 | Gundling |
| 9,523,115 B2 | 12/2016 | Birnboim |
| D775,953 S | 1/2017 | Ruthe-Steinsiek |
| D777,111 S | 1/2017 | Zantout et al. |
| 9,732,376 B2 | 8/2017 | Oyler et al. |
| 9,757,179 B2 | 9/2017 | Formica |
| D811,882 S | 3/2018 | Gundersen |
| 10,000,795 B2 | 6/2018 | Birnboim et al. |
| D843,834 S | 3/2019 | Gundersen |
| D850,647 S | 6/2019 | Jackson et al. |
| 10,435,735 B2 | 10/2019 | Birnboim et al. |
| 12,217,393 B2 * | 2/2025 | Girshick .............. G06T 11/60 |
| 2001/0041327 A1 | 11/2001 | Gross |
| 2002/0032687 A1 | 3/2002 | Huff |
| 2003/0089627 A1 | 5/2003 | Chelles et al. |
| 2003/0172065 A1 | 9/2003 | Sorenson et al. |
| 2004/0132091 A1 | 7/2004 | Ramsey et al. |
| 2005/0147947 A1 | 7/2005 | Cookson et al. |
| 2005/0267903 A1 | 12/2005 | Golze |
| 2006/0025929 A1 | 2/2006 | Eglington |
| 2006/0201948 A1 | 9/2006 | Ellson et al. |
| 2007/0168368 A1 | 7/2007 | Stone |
| 2007/0170142 A1 | 7/2007 | Cho |
| 2007/0178500 A1 | 8/2007 | Martin et al. |
| 2007/0218429 A1 | 9/2007 | Kolo et al. |
| 2007/0239802 A1 | 10/2007 | Razdow et al. |
| 2008/0027656 A1 | 1/2008 | Parida |
| 2008/0068401 A1 | 3/2008 | Albrecht et al. |
| 2008/0081331 A1 | 4/2008 | Myres et al. |
| 2008/0108027 A1 | 5/2008 | Sallin |
| 2008/0189047 A1 | 8/2008 | Wong et al. |
| 2008/0270431 A1 | 10/2008 | Garbero |
| 2009/0024060 A1 | 1/2009 | Darrigrand et al. |
| 2009/0216213 A1 | 8/2009 | Muir et al. |
| 2010/0049736 A1 | 2/2010 | Rolls et al. |
| 2010/0099149 A1 | 4/2010 | Birnboim et al. |
| 2010/0223281 A1 | 9/2010 | Hon et al. |
| 2010/0258457 A1 | 10/2010 | Seelhofer |
| 2011/0020195 A1 | 1/2011 | Luotola |
| 2011/0207621 A1 | 8/2011 | Montagu et al. |
| 2011/0212002 A1 | 9/2011 | Curry et al. |
| 2012/0024861 A1 | 2/2012 | Otsuka et al. |
| 2012/0024862 A1 | 2/2012 | Otsuka et al. |
| 2012/0046574 A1 | 2/2012 | Skakoon |
| 2012/0061392 A1 | 3/2012 | Beach et al. |
| 2013/0092690 A1 | 4/2013 | Skakoon |
| 2013/0149707 A1 | 6/2013 | Sorenson et al. |
| 2013/0164738 A1 | 6/2013 | Becker et al. |
| 2014/0006433 A1 | 1/2014 | Hon et al. |
| 2014/0025308 A1 | 1/2014 | Jorde et al. |
| 2014/0278138 A1 | 9/2014 | Barber et al. |
| 2014/0316302 A1 | 10/2014 | Nonnemacher et al. |
| 2015/0056716 A1 | 2/2015 | Oyler et al. |
| 2016/0262679 A1 | 9/2016 | Ivosevic et al. |
| 2016/0350479 A1 | 12/2016 | Han et al. |
| 2017/0001191 A1 | 1/2017 | Biadillah et al. |

(56) References Cited

U.S. PATENT DOCUMENTS

| | | |
|---|---|---|
| 2017/0072393 A1 | 3/2017 | Jackson et al. |
| 2017/0130219 A1 | 5/2017 | Birnboim et al. |
| 2017/0166955 A1 | 6/2017 | Birnboim et al. |
| 2017/0213127 A1 | 7/2017 | Duncan |
| 2017/0226469 A1 | 8/2017 | Birnboim et al. |
| 2017/0228498 A1 | 8/2017 | Hon et al. |
| 2017/0277827 A1 | 9/2017 | Granka et al. |
| 2017/0329891 A1 | 11/2017 | Macpherson et al. |
| 2019/0151842 A1 | 5/2019 | Williams et al. |
| 2019/0194742 A1* | 6/2019 | Wu .................. G16B 40/00 |
| 2019/0210778 A1 | 7/2019 | Muir et al. |
| 2019/0358628 A1 | 11/2019 | Curry et al. |
| 2020/0135296 A1* | 4/2020 | Girshick ............ G16B 40/20 |
| 2020/0273542 A1 | 8/2020 | Song et al. |
| 2020/0380015 A1 | 12/2020 | Gray |
| 2021/0082167 A1* | 3/2021 | Jewett ................ G06N 5/02 |

FOREIGN PATENT DOCUMENTS

| | | |
|---|---|---|
| KR | 10-2009-0022519 A | 3/2009 |
| WO | WO 2010/077336 A1 | 7/2010 |

OTHER PUBLICATIONS

Li, X. et al. "Efficient Identification of Identical-by-Descent Status in Pedigrees with Many Untyped Individuals." vol. 26, No. 12, Jun. 2010, pp. i191-i198.

Meulenbelt I. et al. "High-Yield Noninvasive Human Genomic DNA Isolation Method for Genetic Studies in Geographically Dispersed Families and Populations." American Journal of Human Genetics, vol. 57, No. 5, Nov. 1995, pp. 1252-1254.

* cited by examiner

FILTERING INDIVIDUAL DATASETS IN A DATABASE

CROSS REFERENCE TO RELATED APPLICATIONS

This application claims the benefit of U.S. Provisional Application No. 63/332,811, filed Apr. 20, 2022, which is hereby incorporated in its entirety by reference.

FIELD

The disclosed embodiments relate to linking individual datasets in a genetic database.

BACKGROUND

A large-scale database such as a genealogy database can include billions of data records. This type of database may allow users to build family trees, research their family history, and make meaningful discoveries about the lives of their ancestors. Users may try to identify relatives with datasets in the database. However, identifying relatives in the sheer amount of data is not a trivial task. Datasets associated with different individuals may not be connected without a proper determination of how the datasets are related. Comparing a large number of datasets without a concrete strategy may also be computationally infeasible because each dataset may also include a large number of data bits. Given an individual dataset and a database with datasets that are potentially related to the individual dataset, it is often challenging to identify a dataset in the database that is associated with the individual dataset.

Users of the genealogy database can easily get "lost" in the amount of family trees and potential relatives in the genealogy database. A new user may struggle to establish connections between their immediate family tree and more distant family trees. Users with established family trees may similarly struggle to connect their family tree with extended, distant family trees. Users of the genealogy database may additionally lack the time or expertise to conduct the thorough genetic and genealogical research required to discover missing pieces of a family tree. Users can understand the direct relationships between themselves and close relative in their family trees, but many users struggle to track family tree relationships throughout several generations. Therefore, it can be difficult for users to establish complex and large family trees.

SUMMARY

Disclosed herein relates to various methods, systems, and non-transitory computer readable mediums with embodiments that identify common ancestors of individuals in a genetic database. In some embodiments, a genetic database receives a target individual genetic dataset associated with a target individual. The genetic database identifies a plurality of matched individuals who genetically match with the target individual. The matched individuals may be related by identity by descent (IBD). In some embodiments, the matched individual is identified by receiving a candidate genetic dataset of a candidate individual and identifying matched genetic segments between the candidate individual and the target individual. The genetic database may measure a total length of the matched genetic segments in centimorgans (cM) and classify the candidate individual as the matched individual based on the length being above a threshold.

The genetic database identifies a plurality of potential ancestors who are potential common ancestors between the target individual and one of the matched individuals. The potential common ancestors may be documented in a family tree of one of the matched individuals. The genetic database inputs a set of features related to the target individual to a machine learning model and filters the plurality of potential common ancestors using the machine learning model. In some embodiments, the set of features includes the total length of the matched segments in cM. The set of features may include a generation difference between a potential common ancestor and a matched individual. The set of features may include an age difference between the target individual and a potential common ancestor. In some embodiments, the set of features includes a percentage of descendants in a family tree of a potential common ancestor who are matched individuals of the target individual. By filtering the potential common ancestors, the genetic database identifies a subset of the potential common ancestors of the target individual. The subset of potential common ancestors may be the potential common ancestors most likely to have a familial relationship with the target individual. In some embodiments, the subset of potential common ancestors are more likely to be direct-line ancestors of the target individual than other potential common ancestors that are filtered out by the machine learning model.

In some embodiments, the machine learning model used to filter the plurality of potential common ancestors may be a supervised learning model. The machine learning model may be configured, in embodiments, to provide a label that a potential common ancestor is a direct-line ancestor or not. The genetic database may train the machine learning model by generating a plurality of training samples including a set of positive training samples and a set of negative training samples. To generate the training samples, the genetic database may identify a training target individual with a genetic dataset. The genetic database may identify ancestors of the training target individual from the training target individual's family trees. Based on existing family trees, the genetic database determines whether each of the ancestors is a direct-line ancestor of the training target individual or, by contrast, a collateral ancestor In some embodiments, the genetic database assigns a positive label to a particular ancestor responsive to the particular ancestor being a direct-line ancestor of the training target individual. The genetic database may extract training features from the training samples to generate feature vectors, with each feature vector corresponding to one of the training samples. In some embodiments, the genetic database inputs the feature vectors to the machine learning model. The genetic database may use the machine learning model to predict labels of one or more ancestors in the training samples. The genetic database determines an objective function that compares the predicted labels to actual labels of the training samples, and adjusts the weights of the machine learning model based on the objective function.

Figure 1:
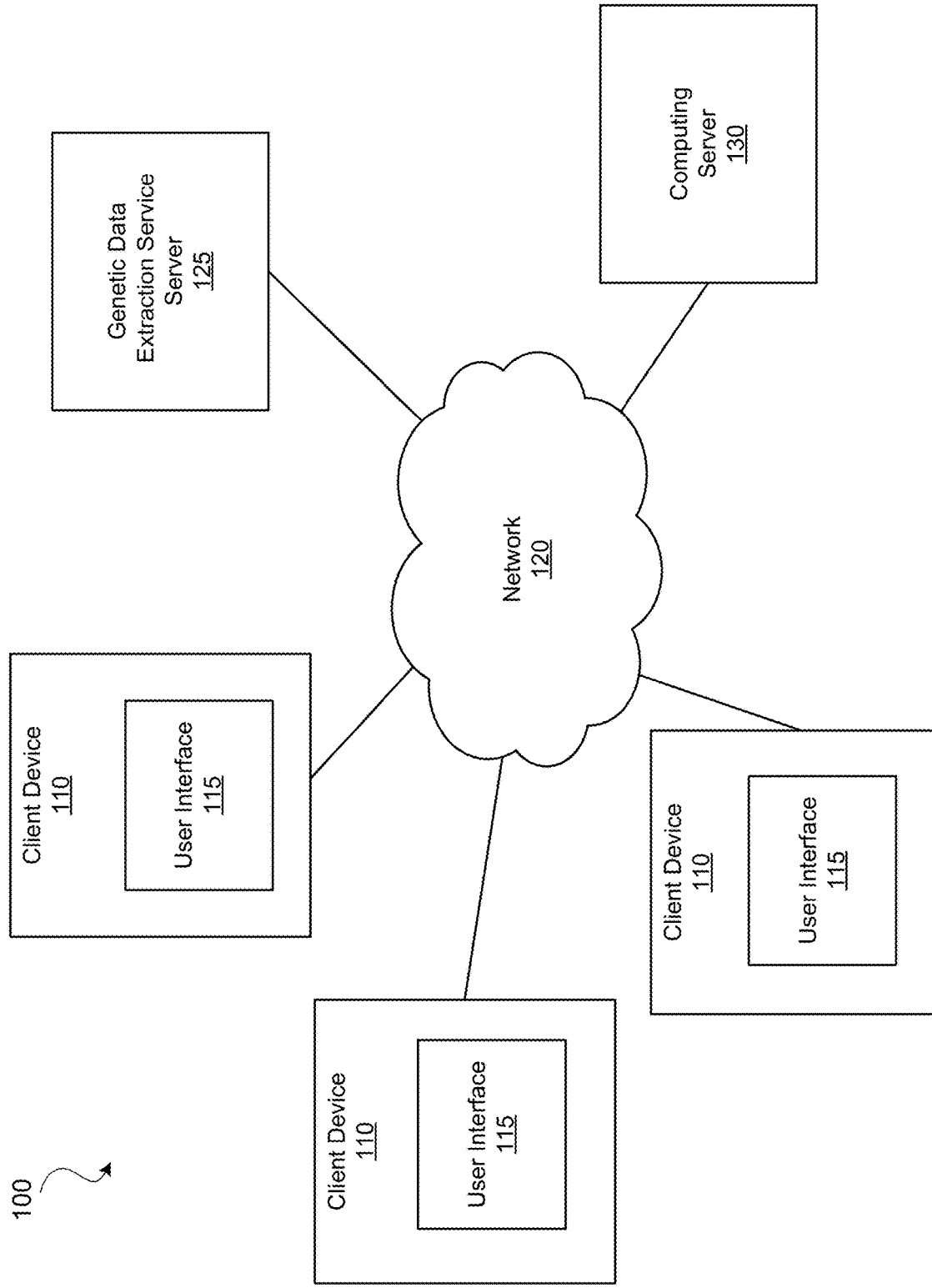
FIG. 1 illustrates a diagram of a system environment of an example computing system, in accordance with some embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

The figures (FIGs.) and the following description relate to preferred embodiments by way of illustration only. One of skill in the art may recognize alternative embodiments of the structures and methods disclosed herein as viable alternatives that may be employed without departing from the principles of what is disclosed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

A system, method, and/or computer-program product is described to enable users of a genetic database to build family trees. The system includes determining a matched individual for a target individual and a common ancestor from which to determine candidate family trees. In some embodiments, the matched individual is identified based on features in the target individual's genetic dataset. For example, the matched individual may share genetic similarities with the target individual. The common ancestor is determined from the matched individual's family tree(s), and is selected based on the target individual's features. The target individual's features may include a generation difference between the target individual and the potential common ancestor and an age difference. The features may include a percentage of descendents in a family tree of the potential common ancestor who are matched individuals of the target individual. The features may additionally include the total length of matched segments in cM.

The genetic database may provide recommended family trees to the target individual. For example, the genetic database might provide a candidate family tree with the target individual in a proposed placement on the tree. The target individual can use the candidate family tree as a starting point to build on. In some embodiments, the genetic database may offer recommendations for the target individual to extend an already-established family tree with identified common ancestors. The genetic databset may identify matched individuals and common ancestors that the target individual had not included in their family tree. The target individual can use these recommendations to extend their family tree to include previously unknown or unincluded relatives. These improvements advantageously provide for more-intuitive, faster, less-costly, and more-rewarding user experiences while reducing the cost and complexity of generating family trees.

Example System Environment

FIG. 1 illustrates a diagram of a system environment 100 of an example computing server 130, in accordance with some embodiments. The system environment 100 shown in FIG. 1 includes one or more client devices 110, a network 120, a genetic data extraction service server 125, and a computing server 130. In various embodiments, the system environment 100 may include fewer or additional components. The system environment 100 may also include different components.

The client devices 110 are one or more computing devices capable of receiving user input as well as transmitting and/or receiving data via a network 120. Example computing devices include desktop computers, laptop computers, personal digital assistants (PDAs), smartphones, tablets, wearable electronic devices (e.g., smartwatches), smart household appliances (e.g., smart televisions, smart speakers, smart home hubs), Internet of Things (IoT) devices or other suitable electronic devices. A client device 110 communicates to other components via the network 120. Users may be customers of the computing server 130 or any individuals who access the system of the computing server 130, such as an online website or a mobile application. In some embodiments, a client device 110 executes an application that launches a graphical user interface (GUI) for a user of the client device 110 to interact with the computing server 130. The GUI may be an example of a user interface 115. A client device 110 may also execute a web browser application to enable interactions between the client device 110 and the computing server 130 via the network 120. In another embodiment, the user interface 115 may take the form of a software application published by the computing server 130 and installed on the user device 110. In yet another embodiment, a client device 110 interacts with the computing server 130 through an application programming interface (API) running on a native operating system of the client device 110, such as IOS or ANDROID.

The network 120 provides connections to the components of the system environment 100 through one or more sub-networks, which may include any combination of local area and/or wide area networks, using both wired and/or wireless communication systems. In some embodiments, a network 120 uses standard communications technologies and/or protocols. For example, a network 120 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 120 may be represented using any suitable format, such as hypertext markup language (HTML) or extensible markup language (XML). In some embodiments, all or some of the communication links of a network 120 may be encrypted using any suitable technique or techniques such as secure sockets layer (SSL), transport layer security (TLS), virtual private networks (VPNs), Internet Protocol security (IPsec), etc. The network 120 also includes links and packet switching networks such as the Internet.

Individuals, who may be customers of a company operating the computing server 130, provide biological samples for analysis of their genetic data. Individuals may also be referred to as users. In some embodiments, an individual uses a sample collection kit to provide a biological sample (e.g., saliva, blood, hair, tissue) from which genetic data is extracted and determined according to nucleotide processing techniques such as amplification and sequencing. Amplification may include using polymerase chain reaction (PCR) to amplify segments of nucleotide samples. Sequencing may include sequencing of deoxyribonucleic acid (DNA) sequencing, ribonucleic acid (RNA) sequencing, etc. Suitable sequencing techniques may include Sanger sequencing and massively parallel sequencing such as various next-generation sequencing (NGS) techniques including whole genome sequencing, pyrosequencing, sequencing by synthesis, sequencing by ligation, and ion semiconductor sequencing. In some embodiments, a set of SNPs (e.g., 300,000) that are shared between different array platforms (e.g., Illumina OmniExpress Platform and Illumina HumanHap 650Y Platform) may be obtained as genetic data. Genetic data extraction service server 125 receives biological samples from users of the computing server 130. The genetic data extraction service server 125 performs sequencing of the biological samples and determines the base pair sequences of the individuals. The genetic data extraction service server 125 generates the genetic data of the individuals based on the sequencing results. The genetic data may include data sequenced from DNA or RNA and may include base pairs from coding and/or noncoding regions of DNA.

The genetic data may take different forms and include information regarding various biomarkers of an individual. For example, in some embodiments, the genetic data may be the base pair sequence of an individual. The base pair sequence may include the whole genome or a part of the genome such as certain genetic loci of interest. In another embodiment, the genetic data extraction service server 125 may determine genotypes from sequencing results, for example by identifying genotype values of single nucleotide polymorphisms (SNPs) present within the DNA. The results in this example may include a sequence of genotypes corresponding to various SNP sites. A SNP site may also be referred to as a SNP loci. A genetic locus is a segment of a genetic sequence. A locus can be a single site or a longer stretch. The segment can be a single base long or multiple bases long. In some embodiments, the genetic data extraction service server 125 may perform data pre-processing of the genetic data to convert raw sequences of base pairs to sequences of genotypes at target SNP sites. Since a typical human genome may differ from a reference human genome at only several million SNP sites (as opposed to billions of base pairs in the whole genome), the genetic data extraction service server 125 may extract only the genotypes at a set of target SNP sites and transmit the extracted data to the computing server 130 as the genetic dataset of an individual. SNPs, base pair sequence, genotype, haplotype, RNA sequences, protein sequences, and phenotypes are examples of biomarkers. In some embodiments, each SNP site may have two readings that are heterozygous.

The computing server 130 performs various analyses of the genetic data, genealogy data, and users' survey responses to generate results regarding the phenotypes and genealogy of users of computing server 130. Depending on the embodiments, the computing server 130 may also be referred to as an online server, a personal genetic service server, a genealogy server, a family tree building server, and/or a social networking system. The computing server 130 receives genetic data from the genetic data extraction service server 125 and stores the genetic data in the data store of the computing server 130. The computing server 130 may analyze the data to generate results regarding the genetics or genealogy of users. The results regarding the genetics or genealogy of users may include the ethnicity compositions of users, paternal and maternal genetic analysis, identification or suggestion of potential family relatives, ancestor information, analyses of DNA data, potential or identified traits such as phenotypes of users (e.g., diseases, appearance traits, other genetic characteristics, and other non-genetic characteristics including social characteristics), etc. The computing server 130 may present or cause the user interface 115 to present the results to the users through a GUI displayed at the client device 110. The results may include graphical elements, textual information, data, charts, and other elements such as family trees.

In some embodiments, the computing server 130 also allows various users to create one or more genealogical profiles of the user. The genealogical profile may include a list of individuals (e.g., ancestors, relatives, friends, and other people of interest) who are added or selected by the user or suggested by the computing server 130 based on the genealogical records and/or genetic records. The user interface 115 controlled by or in communication with the computing server 130 may display the individuals in a list or as a family tree such as in the form of a pedigree chart. In some embodiments, subject to user's privacy setting and authorization, the computing server 130 may allow information generated from the user's genetic dataset to be linked to the user profile and to one or more of the family trees. The users may also authorize the computing server 130 to analyze their genetic dataset and allow their profiles to be discovered by other users.

EXAMPLE COMPUTING SERVER ARCHITECTURE

Figure 2:
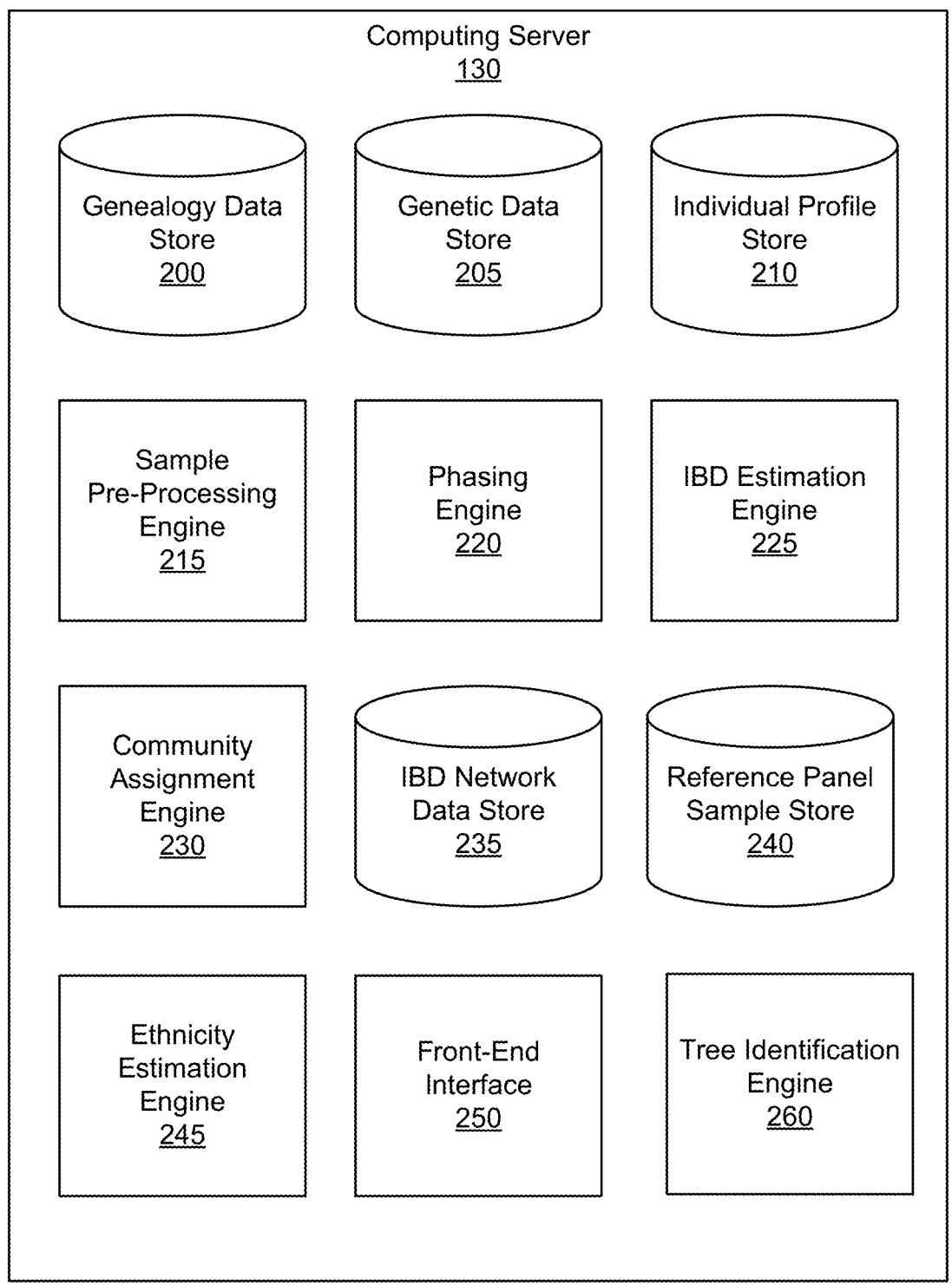
FIG. 2 is a block diagram of an architecture of an example computing system, in accordance with some embodiments.

FIG. 2 is a block diagram of an architecture of an example computing server 130, in accordance with some embodiments. In the embodiment shown in FIG. 2, the computing server 130 includes a genealogy data store 200, a genetic data store 205, an individual profile store 210, a sample pre-processing engine 215, a phasing engine 220, an identity by descent (IBD) estimation engine 225, a community assignment engine 230, an IBD network data store 235, a reference panel sample store 240, an ethnicity estimation engine 245, a front-end interface 250, and a tree management engine 260. The functions of the computing server 130 may be distributed among the elements in a different manner than described. In various embodiments, the computing server 130 may include different components and fewer or additional components. Each of the various data stores may be a single storage device, a server controlling multiple storage devices, or a distributed network that is accessible through multiple nodes (e.g., a cloud storage system).

The computing server 130 stores various data of different individuals, including genetic data, genealogy data, and survey response data. The computing server 130 processes the genetic data of users to identify shared identity-by-descent (IBD) segments between individuals. The genealogy data and survey response data may be part of user profile data. The amount and type of user profile data stored for each user may vary based on the information of a user, which is provided by the user as she creates an account and profile at a system operated by the computing server 130 and continues to build her profile, family tree, and social network at the system and to link her profile with her genetic data. Users may provide data via the user interface 115 of a client device 110. Initially and as a user continues to build her genealogical profile, the user may be prompted to answer questions related to the basic information of the user (e.g., name, date of birth, birthplace, etc.) and later on more advanced questions that may be useful for obtaining additional genealogy data. The computing server 130 may also include survey questions regarding various traits of the users such as the users' phenotypes, characteristics, preferences, habits, lifestyle, environment, etc.

Genealogy data may be stored in the genealogy data store 200 and may include various types of data that are related to tracing family relatives of users. Examples of genealogy data include names (first, last, middle, suffixes), gender, birth locations, date of birth, date of death, marriage information, spouse's information kinships, family history, dates and places for life events (e.g., birth and death), other vital data, and the like. In some instances, family history can take the form of a pedigree of an individual (e.g., the recorded relationships in the family). The family tree information associated with an individual may include one or more specified nodes. Each node in the family tree represents the individual, an ancestor of the individual who might have passed down genetic material to the individual, and the individual's other relatives including siblings, cousins, and offspring in some cases. Genealogy data may also include connections and relationships among users of the computing server 130. The information related to the connections among a user and her relatives that may be associated with a family tree may also be referred to as pedigree data or family tree data.

In addition to user-input data, genealogy data may also take other forms that are obtained from various sources such as public records and third-party data collectors. For example, genealogical records from public sources include birth records, marriage records, death records, census records, court records, probate records, adoption records, obituary records, etc. Likewise, genealogy data may include data from one or more family trees of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, a motor vehicle database, and the like.

Furthermore, the genealogy data store 200 may also include relationship information inferred from the genetic data stored in the genetic data store 205 and information received from the individuals. For example, the relationship information may indicate which individuals are genetically related, how they are related, how many generations back they share common ancestors, lengths and locations of IBD segments shared, which genetic communities an individual is a part of, variants carried by the individual, and the like.

The computing server 130 maintains genetic datasets of individuals in the genetic data store 205. A genetic dataset of an individual may be a digital dataset of nucleotide data (e.g., SNP data) and corresponding metadata. A genetic dataset may contain data on the whole or portions of an individual's genome. The genetic data store 205 may store a pointer to a location associated with the genealogy data store 200 associated with the individual. A DNA tester may be a user who has completed a DNA test that extracts the user's DNA data through the genetic data extraction server 125. The extracted genetic data, which may include genotype or haplotype data, is stored in the genetic data store 205. A genetic dataset may take different forms. In some embodiments, a genetic dataset may take the form of a base pair sequence of the sequencing result of an individual. A base pair sequence dataset may include the whole genome of the individual (e.g., obtained from a whole-genome sequencing) or some parts of the genome (e.g., genetic loci of interest).

In another embodiment, a genetic dataset may take the form of sequences of genetic markers. Examples of genetic markers may include target SNP sites (e.g., allele sites) filtered from the sequencing results. A SNP site that is single base pair long may also be referred to a SNP locus. A SNP site may be associated with a unique identifier. The genetic dataset may be in a form of diploid data that includes a sequencing of genotypes, such as genotypes at the target SNP site, or the whole base pair sequence that includes genotypes at known SNP site and other base pair sites that are not commonly associated with known SNPs. The diploid dataset may be referred to as a genotype dataset or a genotype sequence. Genotype may have a different meaning in various contexts. In one context, an individual's genotype may refer to a collection of diploid alleles of an individual. In other contexts, a genotype may be a pair of alleles present on two chromosomes for an individual at a given genetic marker such as a SNP site.

Genotype data for a SNP site may include a pair of alleles. The pair of alleles may be homozygous (e.g., A-A or G-G) or heterozygous (e.g., A-T, C-T). Instead of storing the actual nucleotides, the genetic data store 205 may store genetic data that are converted to bits. For a given SNP site, oftentimes only two nucleotide alleles (instead of all 4) are observed. As such, a 2-bit number may represent a SNP site. For example, 00 may represent homozygous first alleles, 11 may represent homozygous second alleles, and 01 or 10 may represent heterozygous alleles. A separate library may store what nucleotide corresponds to the first allele and what nucleotide corresponds to the second allele at a given SNP site.

A diploid dataset may also be phased into two sets of haploid data, one corresponding to a first parent side and another corresponding to a second parent side. The phased datasets may be referred to as haplotype datasets or haplotype sequences. Similar to genotype, haplotype may have a different meaning in various contexts. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

The individual profile store 210 stores profiles and related metadata associated with various individuals appeared in the computing server 130. A computing server 130 may use unique individual identifiers to identify various users and other non-users that might appear in other data sources such as ancestors or historical persons who appear in any family tree or genealogy database. A unique individual identifier may be a hash of certain identification information of an individual, such as a user's account name, user's name, date of birth, location of birth, or any suitable combination of the information. The profile data related to an individual may be stored as metadata associated with an individual's profile. For example, the unique individual identifier and the metadata may be stored as a key-value pair using the unique individual identifier as a key.

An individual's profile data may include various kinds of information related to the individual. The metadata about the individual may include one or more pointers associating genetic datasets such as genotype and phased haplotype data of the individual that are saved in the genetic data store 205. The metadata about the individual may also be individual information related to family trees and pedigree datasets that include the individual. The profile data may further include declarative information about the user that was authorized by the user to be shared and may also include information inferred by the computing server 130. Other examples of information stored in a user profile may include biographic, demographic, and other types of descriptive information such as work experience, educational history, gender, hobbies, or preferences, location and the like. In some embodiments, the user profile data may also include one or more photos of the users and photos of relatives (e.g., ancestors) of the users that are uploaded by the users. A user may authorize the computing server 130 to analyze one or more photos to extract information, such as the user's or relative's appearance traits (e.g., blue eyes, curved hair, etc.), from the photos. The appearance traits and other information extracted from the photos may also be saved in the profile store. In some cases, the computing server may allow users to upload many different photos of the users, their relatives, and even friends. User profile data may also be obtained from other suitable sources, including historical records (e.g., records related to an ancestor), medical records, military records, photographs, other records indicating one or more traits, and other suitable recorded data.

For example, the computing server 130 may present various survey questions to its users from time to time. The responses to the survey questions may be stored at individual profile store 210. The survey questions may be related to various aspects of the users and the users' families. Some survey questions may be related to users' phenotypes, while other questions may be related to environmental factors of the users.

Survey questions may concern health or disease-related phenotypes, such as questions related to the presence or absence of genetic diseases or disorders, inheritable diseases or disorders, or other common diseases or disorders that have a family history as one of the risk factors, questions regarding any diagnosis of increased risk of any diseases or disorders, and questions concerning wellness-related issues such as a family history of obesity, family history of causes of death, etc. The diseases identified by the survey questions may be related to single-gene diseases or disorders that are caused by a single-nucleotide variant, an insertion, or a deletion. The diseases identified by the survey questions may also be multifactorial inheritance disorders that may be caused by a combination of environmental factors and genes. Examples of multifactorial inheritance disorders may include heart disease, Alzheimer's disease, diabetes, cancer, and obesity. The computing server 130 may obtain data on a user's disease-related phenotypes from survey questions about the health history of the user and her family and also from health records uploaded by the user.

Survey questions also may be related to other types of phenotypes such as appearance traits of the users. A survey regarding appearance traits and characteristics may include questions related to eye color, iris pattern, freckles, chin types, finger length, dimple chin, earlobe types, hair color, hair curl, skin pigmentation, susceptibility to skin burn, bitter taste, male baldness, baldness pattern, presence of unibrow, presence of wisdom teeth, height, and weight. A survey regarding other traits also may include questions related to users' taste and smell such as the ability to taste bitterness, asparagus smell, cilantro aversion, etc. A survey regarding traits may further include questions related to users' body conditions such as lactose tolerance, caffeine consumption, malaria resistance, norovirus resistance, muscle performance, alcohol flush, etc. Other survey questions regarding a person's physiological or psychological traits may include vitamin traits and sensory traits such as the ability to sense an asparagus metabolite. Traits may also be collected from historical records, electronic health records and electronic medical records.

The computing server 130 also may present various survey questions related to the environmental factors of users. In this context, an environmental factor may be a factor that is not directly connected to the genetics of the users. Environmental factors may include users' preferences, habits, and lifestyles. For example, a survey regarding users' preferences may include questions related to things and activities that users like or dislike, such as types of music a user enjoys, dancing preference, party-going preference, certain sports that a user plays, video game preferences, etc. Other questions may be related to the users' diet preferences such as like or dislike a certain type of food (e.g., ice cream, egg). A survey related to habits and lifestyle may include questions regarding smoking habits, alcohol consumption and frequency, daily exercise duration, sleeping habits (e.g., morning person versus night person), sleeping cycles and problems, hobbies, and travel preferences.

Additional environmental factors may include diet amount (calories, macronutrients), physical fitness abilities (e.g., stretching, flexibility, heart rate recovery), family type (adopted family or not, has siblings or not, lived with extended family during childhood), property and item ownership (has home or rents, has a smartphone or doesn't, has a car or doesn't).

Surveys also may be related to other environmental factors such as geographical, social-economic, or cultural factors. Geographical questions may include questions related to the birth location, family migration history, town, or city of users' current or past residence. Social-economic questions may be related to users' education level, income, occupations, self-identified demographic groups, etc. Questions related to culture may concern users' native language, language spoken at home, customs, dietary practices, etc. Other questions related to users' cultural and behavioral questions are also possible.

For any survey questions asked, the computing server 130 may also ask an individual the same or similar questions regarding the traits and environmental factors of the ancestors, family members, other relatives or friends of the individual. For example, a user may be asked about the native language of the user and the native languages of the user's parents and grandparents. A user may also be asked about the health history of his or her family members.

In addition to storing the survey data in the individual profile store 210, the computing server 130 may store some responses that correspond to data related to genealogical and genetics respectively to genealogy data store 200 and genetic data store 205.

The user profile data, photos of users, survey response data, the genetic data, and the genealogy data may be subject to the privacy and authorization setting of the users to specify any data related to the users that can be accessed, stored, obtained, or otherwise used. For example, when presented with a survey question, a user may select to answer or skip the question. The computing server 130 may present users from time to time information regarding users' selection of the extent of information and data shared. The computing server 130 also may maintain and enforce one or more privacy settings for users in connection with the access of the user profile data, photos, genetic data, and other sensitive data. For example, the user may pre-authorize the access to the data and may change the setting as wished. The privacy settings also may allow a user to specify (e.g., by opting out, by not opting in) whether the computing server 130 may receive, collect, log, or store particular data associated with the user for any purpose. A user may restrict her data at various levels. For example, on one level, the data may not be accessed by the computing server 130 for purposes other than displaying the data in the user's own profile. On another level, the user may authorize anonymization of her data and participate in studies and research conducted by the computing server 130 such as a large-scale genetic study. On yet another level, the user may turn some portions of her genealogy data public to allow the user to be discovered by other users (e.g., potential relatives) and be connected to one or more family trees. Access or sharing of any information or data in the computing server 130 may also be subject to one or more similar privacy policies. A user's data and content objects in the computing server 130 may also be associated with different levels of restriction. The computing server 130 may also provide various notification features to inform and remind users of their privacy and access settings. For example, when privacy settings for a data entry allow a particular user or other entities to access the data, the data may be described as being "visible," "public," or other suitable labels, contrary to a "private" label.

In some cases, the computing server 130 may have a heightened privacy protection on certain types of data and data related to certain vulnerable groups. In some cases, the heightened privacy settings may strictly prohibit the use, analysis, and sharing of data related to a certain vulnerable group. In other cases, the heightened privacy settings may specify that data subject to those settings require prior approval for access, publication, or other use. In some cases, the computing server 130 may provide the heightened privacy as a default setting for certain types of data, such as genetic data or any data that the user marks as sensitive. The user may opt in to sharing of those data or change the default privacy settings. In other cases, the heightened privacy settings may apply across the board for all data of certain groups of users. For example, if computing server 130 determines that the user is a minor or has recognized that a picture of a minor is uploaded, the computing server 130 may designate all profile data associated with the minor as sensitive. In those cases, the computing server 130 may have one or more extra steps in seeking and confirming any sharing or use of the sensitive data.

The sample pre-processing engine 215 receives and pre-processes data received from various sources to change the data into a format used by the computing server 130. For genealogy data, the sample pre-processing engine 215 may receive data from an individual via the user interface 115 of the client device 110. To collect the user data (e.g., genealogical and survey data), the computing server 130 may cause an interactive user interface on the client device 110 to display interface elements in which users can provide genealogy data and survey data. Additional data may be obtained from scans of public records. The data may be manually provided or automatically extracted via, for example, optical character recognition (OCR) performed on census records, town or government records, or any other item of printed or online material. Some records may be obtained by digitalizing written records such as older census records, birth certificates, death certificates, etc.

The sample pre-processing engine 215 may also receive raw data from genetic data extraction service server 125. The genetic data extraction service server 125 may perform laboratory analysis of biological samples of users and generate sequencing results in the form of digital data. The sample pre-processing engine 215 may receive the raw genetic datasets from the genetic data extraction service server 125. Most of the mutations that are passed down to descendants are related to single-nucleotide polymorphism (SNP). SNP is a substitution of a single nucleotide that occurs at a specific position in the genome. The sample pre-processing engine 215 may convert the raw base pair sequence into a sequence of genotypes of target SNP sites. Alternatively, the pre-processing of this conversion may be performed by the genetic data extraction service server 125. The sample pre-processing engine 215 identifies autosomal SNPs in an individual's genetic dataset. In some embodiments, the SNPs may be autosomal SNPs. In some embodiments, 700,000 SNPs may be identified in an individual's data and may be stored in genetic data store 205. Alternatively, in some embodiments, a genetic dataset may include at least 10,000 SNP sites. In another embodiment, a genetic dataset may include at least 100,000 SNP sites. In yet another embodiment, a genetic dataset may include at least 300,000 SNP sites. In yet another embodiment, a genetic dataset may include at least 1,000,000 SNP sites. The sample pre-processing engine 215 may also convert the nucleotides into bits. The identified SNPs, in bits or in other suitable formats, may be provided to the phasing engine 220 which phases the individual's diploid genotypes to generate a pair of haplotypes for each user.

The phasing engine 220 phases diploid genetic dataset into a pair of haploid genetic datasets and may perform imputation of SNP values at certain sites whose alleles are missing. An individual's haplotype may refer to a collection of alleles (e.g., a sequence of alleles) that are inherited from a parent.

Phasing may include a process of determining the assignment of alleles (particularly heterozygous alleles) to chromosomes. Owing to sequencing conditions and other constraints, a sequencing result often includes data regarding a pair of alleles at a given SNP locus of a pair of chromosomes but may not be able to distinguish which allele belongs to which specific chromosome. The phasing engine 220 uses a genotype phasing algorithm to assign one allele to a first chromosome and another allele to another chromosome. The genotype phasing algorithm may be developed based on an assumption of linkage disequilibrium (LD), which states that haplotype in the form of a sequence of alleles tends to cluster together. The phasing engine 220 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as a training sample because the correct phasing of the child is almost certain by comparing the child's genotypes to the parent's genetic datasets. The haplotype-cluster model may be generated iteratively along with the phasing process with a large number of unphased genotype datasets. The haplotype-cluster model may also be used to impute one or more missing data.

By way of example, the phasing engine 220 may use a directed acyclic graph model such as a hidden Markov model (HMM) to perform the phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing engine 220 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. Pat. No. 10,679,729, entitled "Haplotype Phasing Models," granted on Jun. 9, 2020, describes example embodiments of haplotype phasing.

A phasing algorithm may also generate phasing result that has a long-distance accuracy in terms of haplotype separation. For example, in some embodiments, a jig phasing algorithm may be used, which is described in further detail in U.S. Patent Application Publication No. US 2021/0034647, entitled "Clustering of Matched Segments to Determine Linkage of Dataset in a Database," published on Feb. 4, 2021. For example, the computing server 130 may receive a target individual genotype dataset and a plurality of additional individual genotype datasets that include haplotypes of additional individuals. For example, the additional individuals may be reference panels or individuals who are linked (e.g., in a family tree) to the target individual. The computing server 130 may generate a plurality of sub-cluster pairs of first parental groups and second parental groups. Each sub-cluster pair may be in a window. The window may correspond to a genomic segment and has a similar concept of window used in the ethnicity estimation engine 245 and the rest of the disclosure related to HMMs, but how windows are precisely divided and defined may be the same or different in the phasing engine 220 and in an HMM. Each sub-cluster pair may correspond to a genetic locus. In some embodiments, each sub-cluster pair may have a first parental group that includes a first set of matched haplotype segments selected from the plurality of additional individual datasets and a second parental group that includes a second set of matched haplotype segments selected from the plurality of additional individual datasets. The computing server 130 may generate a super-cluster of a parental side by linking the first parental groups and the second parental groups across a plurality of genetic loci (across a plurality of sub-cluster pairs). Generating the super-cluster of the parental side may include generating a candidate parental side assignment of parental groups across a set of sub-cluster pairs that represent a set of genetic loci in the plurality of genetic loci. The computing server 130 may determine a number of common additional individual genotype datasets that are classified in the candidate parental side assignment. The computing server 130 may determine the candidate parental side assignment to be part of the super-cluster based on the number of common additional individual genotype datasets. Any suitable algorithms may be used to generate the super-cluster, such as a heuristic scoring approach, a bipartite graph approach, or another suitable approach. The computing server 130 may generate a haplotype phasing of the target individual from the super-cluster of the parental side.

The IBD estimation engine 225 estimates the amount of shared genetic segments between a pair of individuals based on phased genotype data (e.g., haplotype datasets) that are stored in the genetic data store 205. IBD segments may be segments identified in a pair of individuals that are putatively determined to be inherited from a common ancestor. The IBD estimation engine 225 retrieves a pair of haplotype datasets for each individual. The IBD estimation engine 225 may divide each haplotype dataset sequence into a plurality of windows. Each window may include a fixed number of SNP sites (e.g., about 100 SNP sites). The IBD estimation engine 225 identifies one or more seed windows in which the alleles at all SNP sites in at least one of the phased haplotypes between two individuals are identical. The IBD estimation engine 225 may expand the match from the seed windows to nearby windows until the matched windows reach the end of a chromosome or until a homozygous mismatch is found, which indicates the mismatch is not attributable to potential errors in phasing or imputation. The IBD estimation engine 225 determines the total length of matched segments, which may also be referred to as IBD segments. The length may be measured in the genetic distance in the unit of centimorgans (cM). A unit of centimorgan may be a genetic length. For example, two genomic positions that are one cM apart may have a 1% chance during each meiosis of experiencing a recombination event between the two positions. The computing server 130 may save data regarding individual pairs who share a length of IBD segments exceeding a predetermined threshold (e.g., 6 cM), in a suitable data store such as in the genealogy data store 200. U.S. Pat. No. 10,114,922, entitled "Identifying Ancestral Relationships Using a Continuous stream of Input," granted on Oct. 30, 2018, and U.S. Pat. No. 10,720,229, entitled "Reducing Error in Predicted Genetic Relationships," granted on Jul. 21, 2020, describe example embodiments of IBD estimation.

Typically, individuals who are closely related share a relatively large number of IBD segments, and the IBD segments tend to have longer lengths (individually or in aggregate across one or more chromosomes). In contrast, individuals who are more distantly related share relatively fewer IBD segments, and these segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity. For example, the IBD affinity may be measured in terms of the length of IBD segments shared between two individuals.

Community assignment engine 230 assigns individuals to one or more genetic communities based on the genetic data of the individuals. A genetic community may correspond to an ethnic origin or a group of people descended from a common ancestor. The granularity of genetic community classification may vary depending on embodiments and methods used to assign communities. For example, in some embodiments, the communities may be African, Asian, European, etc. In another embodiment, the European community may be divided into Irish, German, Swedes, etc. In yet another embodiment, the Irish may be further divided into Irish in Ireland, Irish immigrated to America in 1800, Irish immigrated to America in 1900, etc. The community classification may also depend on whether a population is admixed or unadmixed. For an admixed population, the classification may further be divided based on different ethnic origins in a geographical region.

Community assignment engine 230 may assign individuals to one or more genetic communities based on their genetic datasets using machine learning models trained by unsupervised learning or supervised learning. In an unsupervised approach, the community assignment engine 230 may generate data representing a partially connected undirected graph. In this approach, the community assignment engine 230 represents individuals as nodes. Some nodes are connected by edges whose weights are based on IBD affinity between two individuals represented by the nodes. For example, if the total length of two individuals' shared IBD segments does not exceed a predetermined threshold, the nodes are not connected. The edges connecting two nodes are associated with weights that are measured based on the IBD affinities. The undirected graph may be referred to as an IBD network. The community assignment engine 230 uses clustering techniques such as modularity measurement (e.g., the Louvain method) to classify nodes into different clusters in the IBD network. Each cluster may represent a community. The community assignment engine 230 may also determine sub-clusters, which represent sub-communities. The computing server 130 saves the data representing the IBD network and clusters in the IBD network data store 235.

U.S. Pat. No. 10,223,498, entitled "Discovering Population Structure from Patterns of Identity-By-Descent," granted on Mar. 5, 2019, describes example embodiments of community detection and assignment.

The community assignment engine 230 may also assign communities using supervised techniques. For example, genetic datasets of known genetic communities (e.g., individuals with confirmed ethnic origins) may be used as training sets that have labels of the genetic communities. Supervised machine learning classifiers, such as logistic regressions, support vector machines, random forest classifiers, and neural networks may be trained using the training set with labels. A trained classifier may distinguish binary or multiple classes. For example, a binary classifier may be trained for each community of interest to determine whether a target individual's genetic dataset belongs or does not belong to the community of interest. A multi-class classifier such as a neural network may also be trained to determine whether the target individual's genetic dataset most likely belongs to one of several possible genetic communities.

Reference panel sample store 240 stores reference panel samples for different genetic communities. A reference panel sample is a genetic data of an individual whose genetic data is the most representative of a genetic community. The genetic data of individuals with the typical alleles of a genetic community may serve as reference panel samples. For example, some alleles of genes may be over-represented (e.g., being highly common) in a genetic community. Some genetic datasets include alleles that are commonly present among members of the community. Reference panel samples may be used to train various machine learning models in classifying whether a target genetic dataset belongs to a community, determining the ethnic composition of an individual, and determining the accuracy of any genetic data analysis, such as by computing a posterior probability of a classification result from a classifier.

A reference panel sample may be identified in different ways. In some embodiments, an unsupervised approach in community detection may apply the clustering algorithm recursively for each identified cluster until the sub-clusters contain a number of nodes that are smaller than a threshold (e.g., contains fewer than 1000 nodes). For example, the community assignment engine 230 may construct a full IBD network that includes a set of individuals represented by nodes and generate communities using clustering techniques. The community assignment engine 230 may randomly sample a subset of nodes to generate a sampled IBD network. The community assignment engine 230 may recursively apply clustering techniques to generate communities in the sampled IBD network. The sampling and clustering may be repeated for different randomly generated sampled IBD networks for various runs. Nodes that are consistently assigned to the same genetic community when sampled in various runs may be classified as a reference panel sample. The community assignment engine 230 may measure the consistency in terms of a predetermined threshold. For example, if a node is classified to the same community 95% (or another suitable threshold) of the times whenever the node is sampled, the genetic dataset corresponding to the individual represented by the node may be regarded as a reference panel sample. Additionally, or alternatively, the community assignment engine 230 may select N most consistently assigned nodes as a reference panel for the community.

Other ways to generate reference panel samples are also possible. For example, the computing server 130 may collect a set of samples and gradually filter and refine the samples until high-quality reference panel samples are selected. For example, a candidate reference panel sample may be selected from an individual whose recent ancestors are born at a certain birthplace. The computing server 130 may also draw sequence data from the Human Genome Diversity Project (HGDP). Various candidates may be manually screened based on their family trees, relatives' birth location, and other quality control. Principal component analysis may be used to create clusters of genetic data of the candidates. Each cluster may represent an ethnicity. The predictions of the ethnicity of those candidates may be compared to the ethnicity information provided by the candidates to perform further screening.

The ethnicity estimation engine 245 estimates the ethnicity composition of a genetic dataset of a target individual. The genetic datasets used by the ethnicity estimation engine 245 may be genotype datasets or haplotype datasets. For example, the ethnicity estimation engine 245 estimates the ancestral origins (e.g., ethnicity) based on the individual's genotypes or haplotypes at the SNP sites. To take a simple example of three ancestral populations corresponding to African, European and Native American, an admixed user may have nonzero estimated ethnicity proportions for all three ancestral populations, with an estimate such as [0.05, 0.65, 0.30], indicating that the user's genome is 5% attributable to African ancestry, 65% attributable to European ancestry and 30% attributable to Native American ancestry. The ethnicity estimation engine 245 generates the ethnic composition estimate and stores the estimated ethnicities in a data store of computing server 130 with a pointer in association with a particular user.

In some embodiments, the ethnicity estimation engine 245 divides a target genetic dataset into a plurality of windows (e.g., about 1000 windows). Each window includes a small number of SNPs (e.g., 300 SNPs). The ethnicity estimation engine 245 may use a directed acyclic graph model to determine the ethnic composition of the target genetic dataset. The directed acyclic graph may represent a trellis of an inter-window hidden Markov model (HMM). The graph includes a sequence of a plurality of node groups. Each node group, representing a window, includes a plurality of nodes. The nodes represent different possibilities of labels of genetic communities (e.g., ethnicities) for the window. A node may be labeled with one or more ethnic labels. For example, a level includes a first node with a first label representing the likelihood that the window of SNP sites belongs to a first ethnicity and a second node with a second label representing the likelihood that the window of SNPs belongs to a second ethnicity. Each level includes multiple nodes so that there are many possible paths to traverse the directed acyclic graph.

The nodes and edges in the directed acyclic graph may be associated with different emission probabilities and transition probabilities. An emission probability associated with a node represents the likelihood that the window belongs to the ethnicity labeling the node given the observation of SNPs in the window. The ethnicity estimation engine 245 determines the emission probabilities by comparing SNPs in the window corresponding to the target genetic dataset to corresponding SNPs in the windows in various reference panel samples of different genetic communities stored in the reference panel sample store 240. The transition probability between two nodes represents the likelihood of transition from one node to another across two levels. The ethnicity estimation engine 245 determines a statistically likely path, such as the most probable path or a probable path that is at least more likely than 95% of other possible paths, based on the transition probabilities and the emission probabilities. A suitable dynamic programming algorithm such as the Viterbi algorithm or the forward-backward algorithm may be used to determine the path. After the path is determined, the ethnicity estimation engine 245 determines the ethnic composition of the target genetic dataset by determining the label compositions of the nodes that are included in the determined path. U.S. Pat. No. 10,558,930, entitled "Local Genetic Ethnicity Determination System," granted on Feb. 11, 2020 and U.S. Pat. No. 10,692,587, granted on Jun. 23, 2020, entitled "Global Ancestry Determination System" describe different example embodiments of ethnicity estimation.

The front-end interface 250 displays various results determined by the computing server 130. The results and data may include the IBD affinity between a user and another individual, the community assignment of the user, the ethnicity estimation of the user, phenotype prediction and evaluation, genealogy data search, family tree and pedigree, relative profile and other information. The front-end interface 250 may allow users to manage their profile and data trees (e.g., family trees). The users may view various public family trees stored in the computing server 130 and search for individuals and their genealogy data via the front-end interface 250. The computing server 130 may suggest or allow the user to manually review and select potentially related individuals (e.g., relatives, ancestors, close family members) to add to the user's data tree. The front-end interface 250 may be a graphical user interface (GUI) that displays various information and graphical elements. The front-end interface 250 may take different forms. In one case, the front-end interface 250 may be a software application that can be displayed on an electronic device such as a computer or a smartphone. The software application may be developed by the entity controlling the computing server 130 and be downloaded and installed on the client device 110. In another case, the front-end interface 250 may take the form of a webpage interface of the computing server 130 that allows users to access their family tree and genetic analysis results through web browsers. In yet another case, the front-end interface 250 may provide an application program interface (API).

The tree management engine 260 performs computations and other processes related to users' management of their data trees such as family trees. The tree management engine 260 may allow a user to build a data tree from scratch or to link the user to existing data trees. In some embodiments, the tree management engine 260 may suggest a connection between a target individual and a family tree that exists in the family tree database by identifying potential family trees for the target individual and identifying one or more most probable positions in a potential family tree. A user (target individual) may wish to identify family trees to which he or she may potentially belong. Linking a user to a family tree or building a family may be performed automatically, manually, or using techniques with a combination of both. In an embodiment of an automatic tree matching, the tree management engine 260 may receive a genetic dataset from the target individual as input and search related individuals that are IBD-related to the target individual. The tree management engine 260 may identify common ancestors. Each common ancestor may be common to the target individual and one of the related individuals. The tree management engine 260 may in turn output potential family trees to which the target individual may belong by retrieving family trees that include a common ancestor and an individual who is IBD-related to the target individual. The tree management engine 260 may further identify one or more probable positions in one of the potential family trees based on information associated with matched genetic data between the target individual and those in the potential family trees through one or more machine learning models or other heuristic algorithms. For example, the tree management engine 260 may try putting the target individual in various possible locations in the family tree and determine the highest probability position(s) based on the genetic dataset of the target individual and genetic datasets available for others in the family tree and based on genealogy data available to the tree management engine 260. The tree management engine 260 may provide one or more family trees from which the target individual may select. For a suggested family tree, the tree management engine 260 may also provide information on how the target individual is related to other individuals in the tree. In a manual tree building, a user may browse through public family trees and public individual entries in the genealogy data store 200 and individual profile store 210 to look for potential relatives that can be added to the user's family tree. The tree management engine 260 may automatically search, rank, and suggest individuals for the user conduct manual reviews as the user makes progress in the front-end interface 250 in building the family tree.

As used herein, "pedigree" and "family tree" may be interchangeable and may refer to a family tree chart or pedigree chart that shows, diagrammatically, family information, such as family history information, including parentage, offspring, spouses, siblings, or otherwise for any suitable number of generations and/or people, and/or data pertaining to persons represented in the chart. U.S. Pat. No. 11,429,615, entitled "Linking Individual Datasets to a Database," granted on Aug. 30, 2022, describes example embodiments of how an individual may be linked to existing family trees.

FAMILY TREE IDENTIFICATION

Figure 3A:
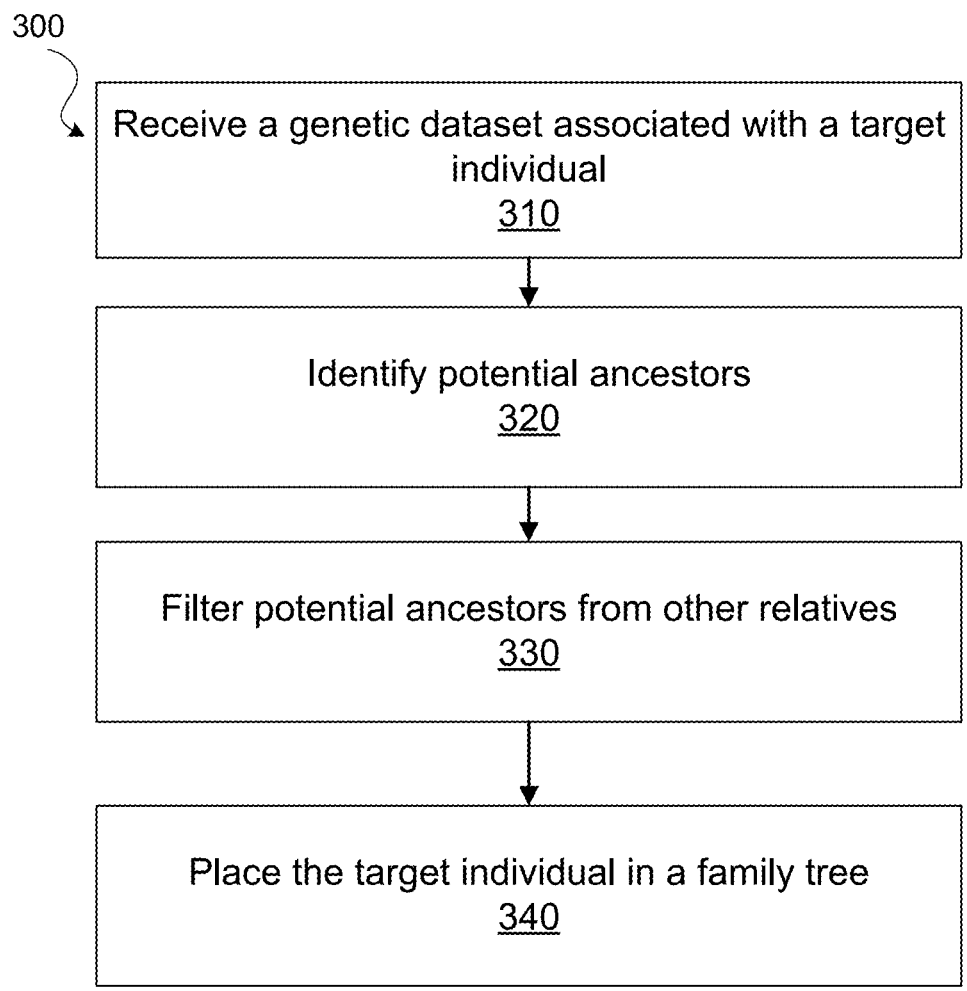
FIG. 3A is a flow chart illustrating an example process that includes various example stages for linking a target individual to a family tree, in accordance with some embodiments.

FIG. 3A is a flowchart depicting an example process 300 for linking a target individual to a family tree, in accordance with some embodiments. The example process 300 assists users with building their family tree on the computing server 130. The process 300 may be part of the process performed by one or more engines of the computing server 130, such as the tree identification engine 260. The process 300 may be embodied as a software algorithm that may be stored as computer instructions that are executable by one or more processors. The instructions, when executed by the processors, cause the processors to perform various steps in the process 300. In various embodiments, the process may include additional, fewer, or different steps. While various steps in process 300 may be discussed with the use of computing server 130, each step may be performed by a different computing device.

In some embodiments, the computing server 130 receives 310 a genetic dataset associated with a target individual. The target individual may be an individual who has taken a DNA test with the company operating the computing server 130 or who has transferred their DNA data and/or test results between companies or providers. The genetic dataset may be generated through the process described in the genetic data extraction service server 125. The genetic dataset may contain genetic data including DNA sequences of the target individual. The genetic dataset may be received from the genetic data store 205. The genetic dataset may be further processed by one or more engines of computing server 130, such as the sample pre-processing engine 215, phasing engine 220, and IBD estimation engine 225. Various processing techniques are discussed above with reference to FIG. 1 and FIG. 2.

Continuing with reference to FIG. 3A, the computing server 130 identifies 320 potential ancestors for the target individual. Identifying 320 potential ancestors may include identifying one or more matched individuals who share a genetic match with the target individual. The computing server 130 identifies one or more matched individuals' ancestors who are potential common ancestors shared by the target individual and one of the matched individuals. An ancestor of the matched individual may be documented in the matched individual's family tree and may be identified as a potential common ancestor. For example, a potential common ancestor may be a direct-line ancestor of a matched individual, such as a grandfather. However, the computing server 130 may not be certain whether a direct-line ancestor of the matched individual is in fact a common ancestor between the target individual and the matched individual. Whether the target individual fits into the matched individual's family tree and how the target individual might fit into the matched individual's family tree may not yet be clear to the computing server 130. Further information for how potential common ancestors may be identified are described in FIG. 4.

Continuing with reference to FIG. 3A, the computing server 130 may filter 330 potential common ancestors from other relatives or unrelated individuals. The filtering criteria may be defined by the computing server 130. In some embodiments, potential common ancestors are filtered to select ancestors who are predicted to be direct-line ancestors of the target individual. Predicted non-blood relatives and collateral-line relatives (e.g., people that are related to the target individual but not through a direct line) are filtered. Whether a potential common ancestor is a direct-line ancestor of the target individual, a collateral-line relative, or a non-blood relative may be uncertain based on the available data at this stage if the target individual does not have a family tree or has a limited family tree. The computing server 130 may convert available data related to the target individual to a set of features. The set of features may be input into a machine learning model to predict whether a potential common ancestor should be filtered out or not. Further details for filtering 330 and the machine learning training and predictions are discussed with reference to FIG. 4 through FIG. 10.

The computing server 130 may place 340 the target individual in a family tree. Placing 340 the target individual includes determining whether the target individual belongs to a family tree and identifying one or more candidate locations where the target individual may fit in the family tree. The placement of the target individual is based on the genetic and genealogical relationship between the target individual and each of the individuals in the family tree. The determination of whether the target individual belongs to a family tree may be based on a manual process or an automatic algorithm. For example, in a manual process, the computing server 130 may present, via a graphical user interface, a family tree to the target individual and have the target individual manually determine whether he or she should belong to the family tree. To automatically assign the target individual to a position in a family tree, the computing server 130 may perform various operations and generate multiple candidate family trees. The candidate family trees are examined by one or more algorithms to determine the likelihood that a candidate family tree is correct. Examples of various algorithms for placing a target individual in a family tree are further discussed below with reference to FIG. 11 through FIG. 13.

The computing server 130 may use the process 300 to identify one or more family trees to which a target individual may belong. The computing server may additionally use the process 300 to suggest candidate placements in the family trees for the target individual. In some embodiments, the computing server 130 may use the process 300 to help the target individual to identify potential family trees, especially for target individuals who are new to the system (e.g., new users of computing server 130). The computing server 130 may identify potential family trees by automatically identifying one or more existing family trees into which the target individual may fit. This advantageously allows users who do not already have a family tree in the system to provide a genetic sample and to obtain a family tree without the time, effort, and resources required to build a family tree from scratch. Rather, a user is able to leverage the efforts of existing users who have established a family tree. The ease of providing recommendations for constructing the user's family tree as provided by the disclosed embodiments offers a quickly rewarding and informative experience when using the system.

While target individuals in the process 300 at times may not have a family tree initiated in the computing server 130 or may have barely started building their family tree, the process 300 is not limited to such users. A target individual may also be a well-established user who has a large family tree with the computing server 130. In such cases, the computing server 130 may continue to suggest additional branches to the user with the process 300. Additional use cases are suitable for helping users of the computing server 130 to establish and grow their family trees with the process 300. Upon linking the target individual to a family tree, the computing server 130 may assign metadata to the target individual's dataset to serve as an indication that the target individual's dataset is linked to the family tree.

Figure 3B:
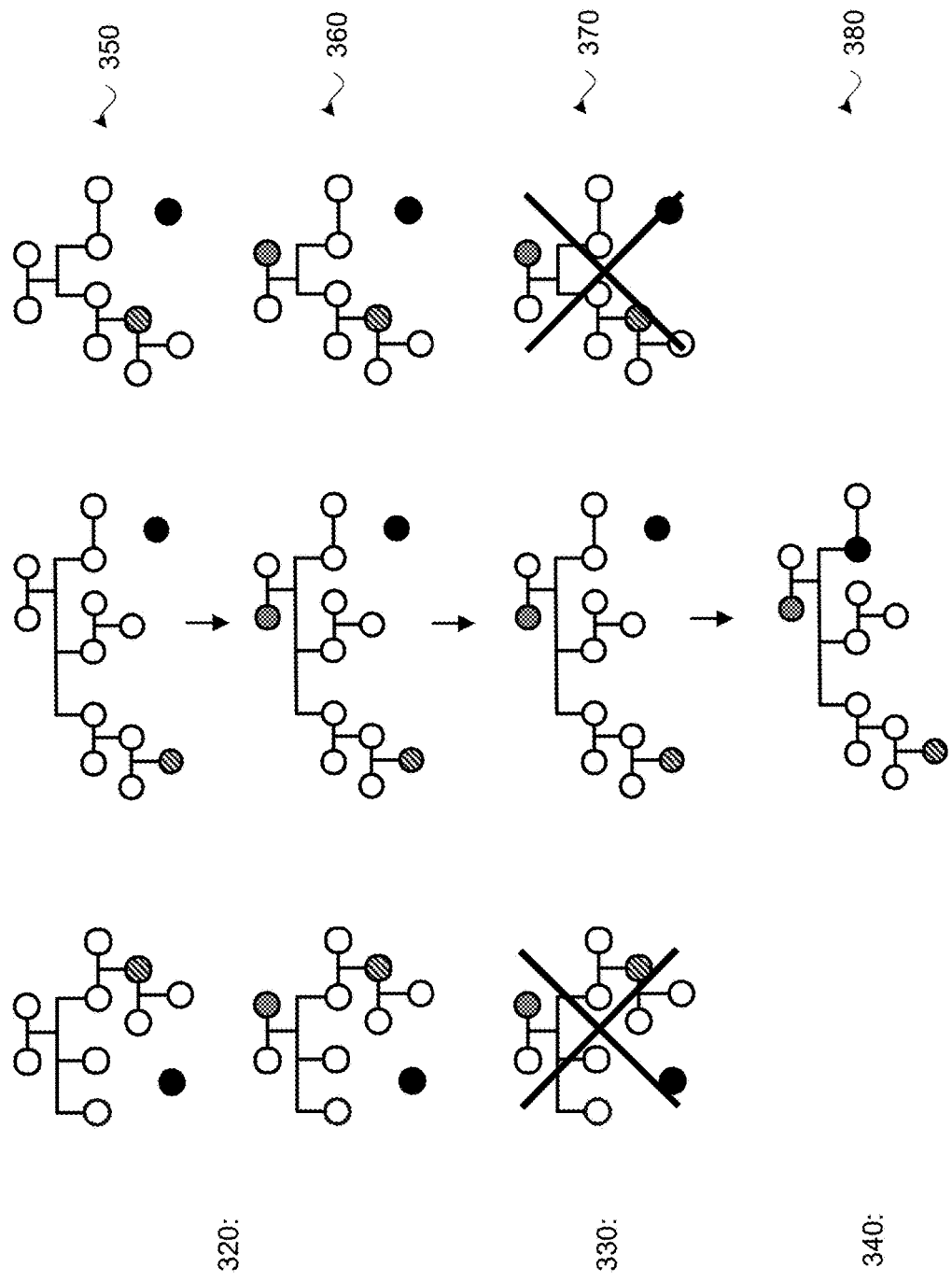
FIG. 3B is a conceptual diagram illustrating the process graphically, in accordance with some embodiments.

FIG. 3B is a conceptual diagram that graphically illustrates the process 300, in accordance with some embodiments. Each family tree shown in FIG. 3B is an example for illustrative purposes only. An actual family tree often is much larger and includes many more layers. While only three family trees are shown in FIG. 3B, in reality the computing server 130 may process hundreds or even thousands of family trees per target individual. In FIG. 3B, the target individual is represented by a black circle. A matched individual is represented by a striped unit in the family tree. A potential common ancestor is identified by a shaded unit in the family tree.

In stage 320, the computing server 130 may identify potential common ancestors shared by the target individual (a black circle) and the matched individual (a striped circle). The computing server 130 may first identify genetic matches based on the genetic data of the target individual and genetic data of various individuals stored in the computing server 130. A genetic match may be referred to as a matched individual. The matched individual may belong to one or more family trees. The identification of matched individuals and their associated family trees is illustrated in the three candidate family trees 350. The three candidate family trees 350 illustrate the family trees for three matched individuals (in stripes) found in the computing server's database (such as a stitched family tree database and/or a cluster database). The three candidate family trees 350 are the matched individuals' associated family trees. At stage 320, the computing server 130 may not know whether the target individual belongs to any of the candidate family trees. Therefore, the black circle that represents the target individual is placed, or represented, outside of each family tree. The stitched family tree database and/or cluster database used to identify candidate family trees may be distinct databases or components of a single database. The candidate family trees may be configured as described in U.S. Patent Application Publication No. 2020/0257707, entitled "Genealogical Entity Resolution System and Method," published on Aug. 13, 2020, U.S. Patent Application Publication No. 2021/0319003, entitled "System and Method for Genealogical Entity Resolution," published on Oct. 14, 2021, U.S. Patent Application Publication No. 2020/0394188, entitled "Genealogical Tree Tracing and Story Generation," published on Dec. 17, 2020, each of which is incorporated in its reference herein in its entirety.

The computing server 130 may identify potential common ancestors. This process is illustrated in the three candidate common ancestor trees 360. The potential common ancestors identified in the candidate common ancestor trees 360 are represented as grey units in the family trees. Potential common ancestors are selected from the individuals documented in the family trees of the matched individuals. As such, a potential common ancestor may be identified from the family tree of a particular matched individual. For example, a potential common ancestor may be an individual who is above the matched individual (e.g. born before the matched individual) and in a direct line with the matched individual. In some embodiments, the common ancestor may have any relationship to the matched individual and a direct line relationship to the target individual.

In stage 330, the computing server 130 may filter ancestors from other relatives. For example, probable direct-line ancestors of the target individual may be selected, and collateral-line relatives or non-blood relatives are filtered. In some embodiments, at this stage, whether a potential common ancestor is a direct-line ancestor of the target individual may be uncertain based on the available data because the target individual has not been fit to a family tree. Instead, the computing server 130 may use a machine learning model to predict whether a potential common ancestor is a direct-line ancestor of the target individual as opposed to a collateral-line relative or a non-blood relative. In the filtered candidate family trees 370, filtered-out potential common ancestors and/or family trees are represented as being crossed out. The filtered-out candidate family trees may have unlikely direct-line ancestor relationships between the common ancestor and the target individual. While the filtered candidate family trees 370 illustrate only one selected common ancestor, in actual examples there are likely to be more than one selected potential common ancestor.

In stage 340, the computing server 130 may place the target individual in a family tree. In the selected candidate family tree 380, the black circle that represents the target individual is placed in the family tree. In some embodiments, such as the selected candidate family tree 380, the black circle representing the target individual is merged with an existing node in the candidate family tree. In other embodiments, the target individual is added to the candidate family tree as an entirely new node with new connections to existing nodes.

FILTERING POTENTIAL COMMON ANCESTORS

Figure 4:
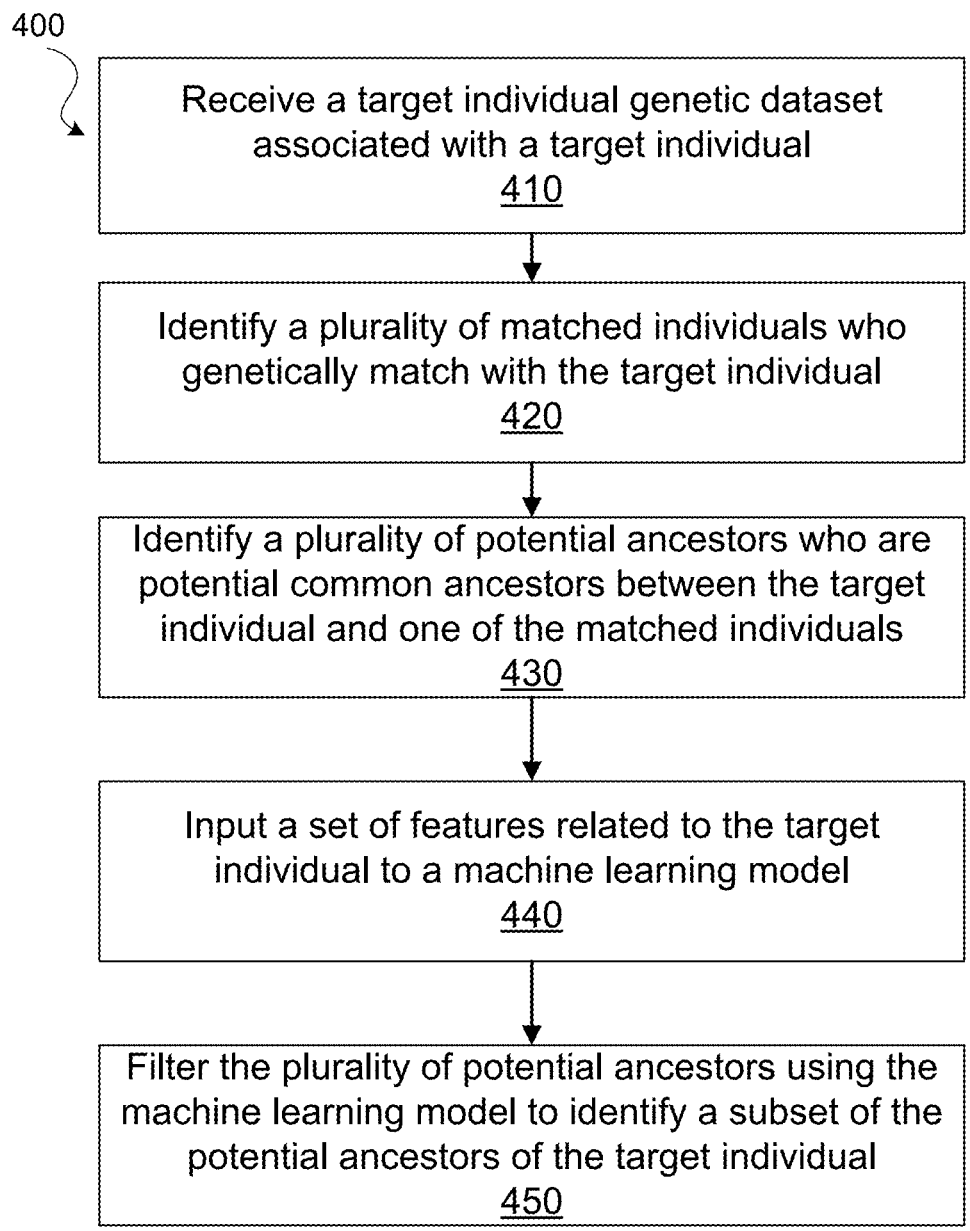
FIG. 4 is a flowchart depicting an example process for filtering potential common ancestors to generate a subset of potential common ancestors, in accordance with some embodiments.

FIG. 4 is a flowchart depicting an example process 400 for filtering potential common ancestors to generate a subset of potential common ancestors, in accordance with some embodiments. The process 400 may correspond to one or more stages in the process 300, such as stage 320 through stage 340. For example, steps 420 and 430 may belong to the stage 320 and steps 440 and 450 may belong to the stage 330.

In some embodiments, the computing server 130 receives 410 a target individual genetic dataset. The target individual genetic dataset may be a genetic dataset from the genetic data store 205 that is associated with the target individual. The genetic dataset may contain genetic data including the DNA sequences of the target individual. In some embodiments, the genetic dataset is generated in response to a DNA sample provided by the target individual. The genetic dataset may be generated using the genetic data extraction service server 125 and be further processed by one or more engines of computing server 130 such as the sample pre-processing engine 215, phasing engine 220, and IBD estimation engine 225. Various applicable processing techniques are discussed above with reference to FIG. 1 and FIG. 2.

The computing server 130 may identify 420 a plurality of matched individuals who genetically match with the target individual. The identification of matched individuals may involve using one or more suitable genetic data analysis and comparison techniques to determine the numbers and lengths of shared genetic segments between the target individual and a candidate matched individual. For example, the target individual and a matched individual may be related by identity by descent (IBD). The determination of a matched individual may be performed by one or more engines of the computing server 130 such as the sample pre-processing engine 215, the phasing engine 220, the IBD estimation engine 225, and the community assignment engine 230.

In some embodiments, to identify 420 the plurality of matched individuals, the computing server 130 compares the genetic dataset of the target individual to other genetic datasets stored in the computing server 130. By way of example, the computing server 130 may identify a set of individuals that have genetic data available in the genetic data store 205 as candidate matched individuals. Candidate individual datasets are genetic datasets corresponding to those candidate matched individuals. The computing server 130 may receives a candidate individual dataset for each a candidate matched individual.

From the candidate individual datasets, the computing server 130 may identify one or more DNA matches for the target individual based on shared IBD information between the target individual and a candidate individual. The computing server 130 may identify matched genetic segments between the candidate individual genetic dataset and the target individual, such as a certain amount of IBD segments shared with the target individuals. For example, the computing server 130 may identify a matched individual dataset from the plurality of candidate individual datasets based on matched data bits such as shared genetic data bits. With IBD estimation engine 225, the computing server 130 may determine the lengths of IBD segments shared by the target individual and a candidate individual. The computing server 130 may select one or more candidate individuals as potential DNA matches of the individuals based on one or more suitable selection criteria. For example, the criteria may be the shared IBD segments being higher than a threshold, the two individuals being closely related in an IBD community as determined by community assignment engine 230, or other suitable conditions. The computing server 130 may measure the total length of the matched genetic segments in centimorgan ("cM") and classify a candidate individual as a matched individual in response to the total length exceeding a threshold (e.g., 8 cM or any suitable threshold). In some embodiments, the matched individuals may be further selected based on whether the matched individuals have family trees available in the database. For example, only matched individuals with a certain family tree size (e.g., a certain number of nodes in an associated family tree) are selected in some cases.

The computing server 130 may identify 430 a plurality of potential ancestors who are potential common ancestors between the target individual and one of the matched individuals. For each identified matched individual, the computing server 130 may identify one or more potential common ancestors between the target individual and the matched individual. A potential common ancestor may also be referred to as a potential ancestor, a candidate common ancestor, or a candidate ancestor. The potential common ancestors may be identified through one or more family trees that are related to the target individual and/or the matched individuals. A family tree may be represented as a data tree and a common ancestor may be represented as a parent node, which is a common parent node for both the related individual dataset and the target individual dataset. A common ancestor may be a DNA tester, a user of the computing server, or a historical person in a genealogical record. Since the target individual may not have a family tree or may have a very limited family tree in the computing server 130, potential common ancestors can be mainly selected from family trees of the matched individuals. In some embodiments, at this stage 430, the computing server 130 may not know whether a potential common ancestor is in fact a common ancestor between the target individual and a matched individual, especially because the target individual may not yet have a family tree or may have a limited family tree.

In some cases, the computing server 130 may identify 430 a potential common ancestor through a large-scale network of individuals whose interrelationships are maintained and discovered by the computing server 130. The computing server 130 may construct a large-scale network by concatenating a large number of family trees of different users. Various users, whether having their genetic data stored in computing server 130 or not, may have constructed one or more family trees by using genealogy data store 200 to link individuals such as DNA testers, users of computing servers 130 who have not completed a DNA test, and historical individuals whose records are found in one or more genealogical data records. Based on users' permission to share the information, the computing server 130 may generate a large-scale network of individuals that include DNA testers, other users who have not completed DNA tests, and historical individuals. The large-scale network may include a very large number of people (such as many users of the computing server 130 and many other historical individuals who have been included in one or more family trees of users). The computing server 130 may collect a large number of family trees and link the trees together by identifying one or more common individuals in two or more trees.

As described above, the network may comprise a family tree database and/or a cluster database facilitating interconnections, e.g. stitching or entity resolution, between instantiations of the same person in different trees. Such a database or databases may be those described in U.S. Patent Application Publication No. 2020/0257707, entitled "Genealogical Entity Resolution System and Method," published on Aug. 13, 2020, U.S. Patent Application Publication No. 2021/0319003, entitled "System and Method for Genealogical Entity Resolution," published on Oct. 14, 2021, U.S. Patent Application Publication No. 2020/0394188, entitled "Genealogical Tree Tracing and Story Generation," published on Dec. 17, 2020, for example.

The computing server 130 may input 440 a set of features related to the target individual and/or the matched individual(s) to a machine learning model. The set of features related to the target individual may include data that is directly related to the target individual and data indirectly related to the target individual. For example, data directly related to the target individual may include the genetic data of the target individual, the birth year of the target individual, and other genealogical and vital records of the target individual. Data indirectly related to the target individual may include the genetic data of the matched individual, number and/or length of shared segments between the target individual and the matched individual, data related to the potential common ancestor, age differences between two persons (e.g. an age difference between the target individual and the potential common ancestor(s), birth year of a potential common ancestor, generation difference between two persons, and genealogical and vital records of the matched individual or the potential common ancestor. The set of features may be quantized and converted into a feature vector, which may take the form of a mathematical vector having multiple dimensions. Each dimension may correspond to a quantized feature.

In some embodiments, the set of features includes a generation difference between a potential common ancestor and a matched individual. In embodiments, the generation difference may be retrieved, transformed to, or otherwise provided as a binary logarithm of the number of generations between the potential common ancestor and the matched individual. In some embodiments, the set of features includes an age difference between the target individual and a potential common ancestor. In some embodiments, the set of features includes the potential common ancestor's and the target individual's birth years. In some embodiments, the set of features includes the percentage of descendants of the potential common ancestor in the family tree who are matched individuals of the target individual. In some embodiments, the set of features includes the total length of the shared segments between a target individual and a matched individual. Other features may also be used, such as statistics (mean, medium, maximum, minimum, variance, etc.) of lengths of shared segments in centimorgan between the matched individual and the target individual, statistics of numbers of shared segments between the matched individual and the target individual, statistics of the number of descendants of the potential common ancestor, and statistics of the generation time between a potential common ancestor and the potential common ancestor's descendants who are matched individuals of the target individual. Other features may include any suitable genealogical data of the target individual, matched individual, or the potential common ancestor. The number and the types of features used may be hyperparameters that are determined in training the machine learning model. In some cases, the types of features used that will generate satisfactory performance on the machine learning model may be selected using techniques such as sequential backward selection.

The computing server 130 may filter 450 the plurality of potential common ancestors using the machine learning model to identify a subset of the potential common ancestors of the target individual. The potential common ancestors in the subset of the potential common ancestors are more likely to be direct-line ancestors of the target individual than other potential common ancestors that are filtered out by the machine learning model. The computing server 130 may input the set of features related to the target individual to a machine learning model to filter the potential common ancestors. As discussed, at this stage, how a potential common ancestor is related to the target individual (e.g., whether the potential common ancestor is a direct-line ancestor or not) is unapparent based on the data available to the computing server 130. A machine learning model may be trained to generate an outcome that predicts the likely relationship between a potential common ancestor and the target individual based on the features related to the target individual. The type of outcome may depend on the type of machine learning model trained. In some embodiments, the machine learning model is a binary classifier that generates an outcome that is a label predicting whether a potential common ancestor is a direct-line ancestor or not a direct-line ancestor (e.g. a collateral-line relative or a non-blood relative). In other embodiments, the machine learning model is a multiclass classifier configured to generate a label predicting whether a potential common ancestor is a direct-line ancestor, a collateral-line ancestor, or a non-blood relative. Hence, the set of features representing each possible pair of the target individual and a potential common ancestor may be inputted into the machine learning model. Potential common ancestors that are predicted, e.g. classified, by the machine learning model as direct-line ancestors are selected and the rest are filtered out. In some embodiments, the machine learning model is a scoring model that assigns a score that represents the likelihood of a relationship between the potential common ancestor and the target individual.

Figure 5:
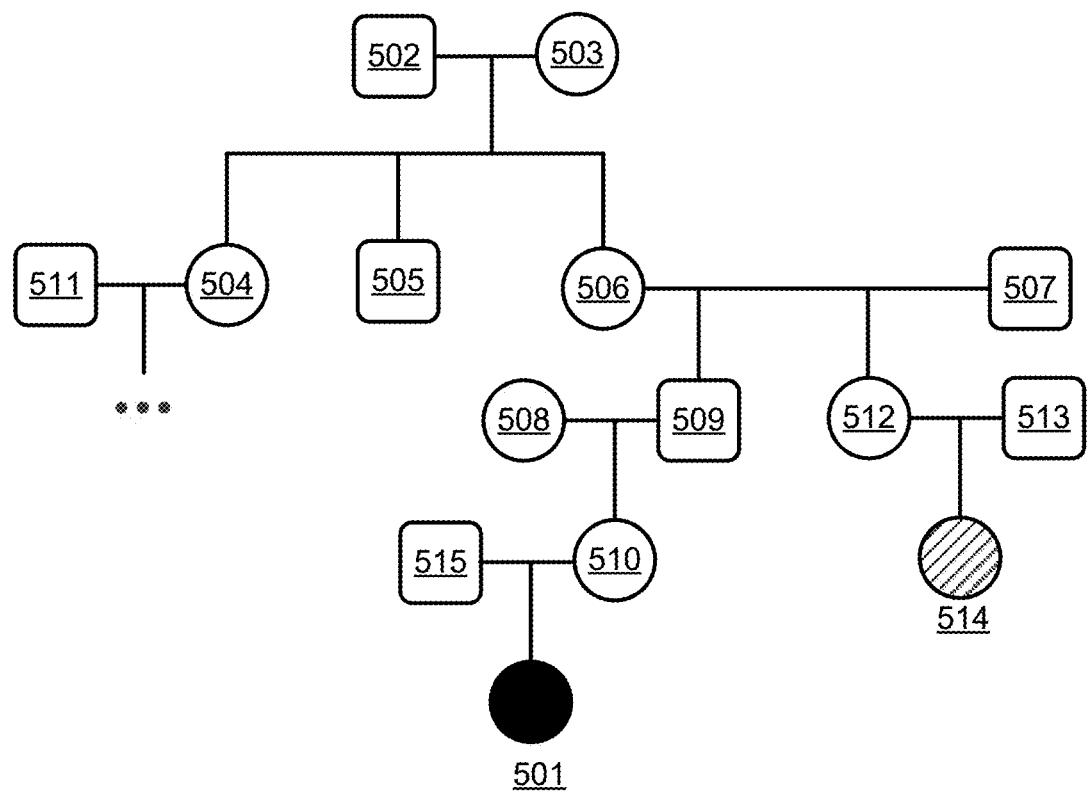
FIG. 5 is a conceptual diagram illustrating a family tree that shows relationships between individuals, in accordance with some embodiments.

FIG. 5 is a conceptual diagram illustrating a family tree 500 that shows relationships between individuals, in accordance with some embodiments. Individual 501 with the black circle may represent a target individual and individual 514 with a striped circle may present a matched individual who is genetically matched with the target individual 501. In this family tree 500, individuals 502, 503, 506, and 507 are direct-line common ancestors of the target individual 501 and matched individual 514. Individuals 511, 504, and 505 are collateral-line relatives such as aunts and uncles. Individuals who are not in the family may be non-blood relatives. A generation time may be a generation difference between two individuals. For example, the generation time between individual 503 and individual 514 is three.

EXAMPLE MACHINE LEARNING MODEL AND TRAINING

Figure 6:
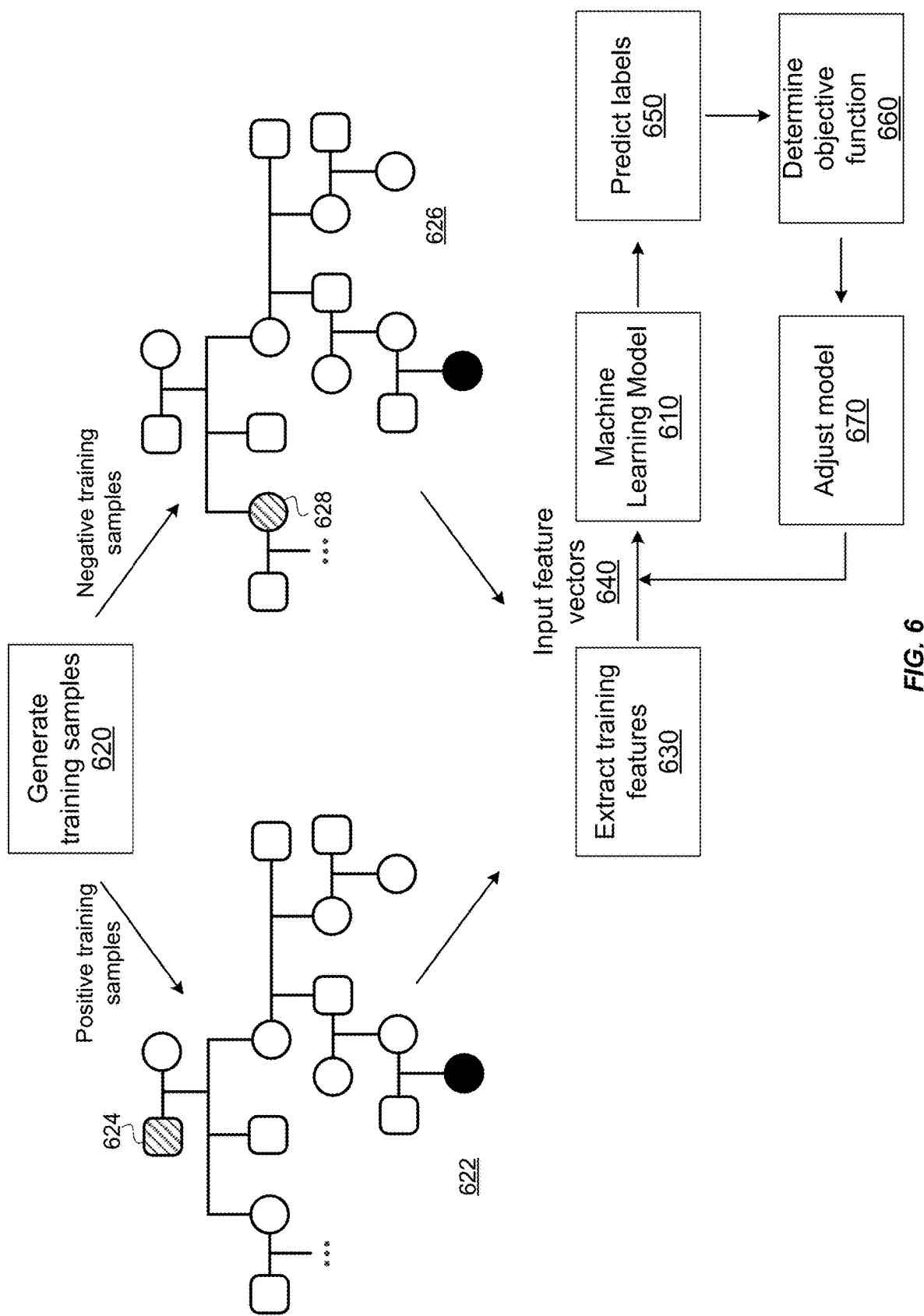
FIG. 6 is a flowchart depicting an example process for training a machine learning model that is used to predict the relationship between a potential common ancestor and a target individual.

FIG. 6 is a flowchart depicting an example process 600 for training a machine learning model 610 that is used to predict the relationship between a potential common ancestor and a target individual. The machine learning model 610 may be used in stage 330 and steps 440 and 450 discussed in FIG. 3A and FIG. 4.

The computing server 130 may apply various machine learning techniques to iteratively train a machine learning model 610. The machine learning model 610, when applied to features related to a target individual, outputs an outcome that predicts the relationship between a target individual and a potential common ancestor, such as a likelihood score that the potential common ancestor is a direct-line ancestor or a binary classification whether the potential common ancestor is a direct-line ancestor.

As part of the training of the machine learning model 610, the computing server 130 may generate 620 multiple training samples. The training samples may include a set of positive training samples of potential common ancestors and a set of negative training samples of potential common ancestors. The positive training samples of potential common ancestors are potential common ancestors that are known to have a defined relationship with a training target individual. The defined relationship may depend on the training goal of the machine learning model 610. For example, in one case, the defined relationship is that the potential common ancestor is a direct-line ancestor of the training target individual.

Generating the training samples may include identifying a training target individual. The computing server 130 may select any suitable individuals in its database as a training target individual. In some embodiments, a training target individual may be an existing individual whose genetic dataset is available to the computing server 130. The training target individual may also have an established family tree in the computing server 130 so that whether a potential common ancestor is a direct-line ancestor can be determined. The potential common ancestors can be selected from the training target individual's family trees and randomly selected from the database of the computing server 130. For example, the computing server 130 may identify ancestors of the training target individual from one or more family trees of the training target individual as some of the potential common ancestors. The computing server 130 may also identify other individuals, in the family trees or not in the family trees, as potential common ancestors. The computing server 130 may determine, based on existing family trees that include the training target individual, whether each of the ancestors is a direct-line ancestor of the training target individual. The computing server 130 may assign a positive label to a particular ancestor in response to the particular ancestor being a direct-line ancestor of the training target individual. For example, in family tree 622, individual 624 may be assigned to a positive training set. The computing server may assign a negative label to another potential common ancestor in response to the other potential common ancestor being a collateral-line relative of the training target individual or there being no documented record that the other potential common ancestor is a direct-line ancestor of the training target individual. For example, in family tree 626, individual 628 may be assigned to a negative training set. The generation of training samples may be repeated for additional training target individuals in the dataset of the computing server 130.

The computing server 130 may extract 630 training features of the training samples to generate feature vectors. Each feature vector may correspond to one of the training samples. The training features may be the features that are discussed in step 440 of process 400 with the values that are generated based on data related to training target individuals. In some embodiments, the computing server 130 may also apply dimensionality reduction (e.g., via linear discriminant analysis (LDA), principal component analysis (PCA), or the like) to reduce the amount of data in the feature vectors to a smaller, more representative set of feature vectors.

The computing server 130 may initiate a machine learning model 610 with one or more weights. The computing server 130 may input 640 the feature vectors to the machine learning model 610 that is untrained or insufficiently trained. In some embodiments, the computing server 130 may use supervised machine learning to train the machine learning model 610, with the feature vectors of the positive training set(s) and the negative training set(s) serving as the inputs. In training, one or more weights, hyperparameters, or other aspects of the machine learning model 610 may be adjusted, as described in detail below. Different types of machine learning models, such as support vector machine (SVM), kernel SVM, gradient boosting including, e.g., XGBoost, neural networks, logistic regression, naïve Bayes, memory-based learning, random forests, bagged trees, decision trees, boosted trees, or neural network, modifications, equivalents, or combinations thereof, or any other suitable modality may be used in different embodiments.

The computing server 130 may use the machine learning model to predict 650 labels of one or more ancestors in the training samples. The machine learning model applies the weights and the nodes with values adjusted at the current iteration (current training epoch) to the feature vector to determine an output. The machine learning model 610, after receiving and applying a feature vector extracted from a training sample, outputs a prediction. Depending on the extent of training, the prediction may be accurate or not. The computing server 130 may repeatedly input different feature vectors to the machine learning model 610 to determine a set of predictions. For example, each output predicts whether a potential common ancestor is a direct-line ancestor of a corresponding training target individual.

The computing server 130 may determine 660 an objective function that compares the predicted labels to actual labels of the training samples. The objective function may generate a metric value that describes the objective goal of the training process. For example, in some embodiments, the objective function may be a loss function that determines the error rate of the machine learning model in the current training iteration. In various embodiments, the error rate may be measured as cross-entropy loss, L1 loss (e.g., the sum of absolute differences between the predicted values and the actual value), L2 loss (e.g., the sum of squared distances, combinations or modifications thereof, or any suitable metric(s)). After different predictions corresponding to different potential common ancestors and/or training target individuals are generated by the machine learning models 610 in step 640, the predictions (e.g., whether a potential common ancestor is a direct-line ancestor) are compared to the actual labels (positive or negative) of the training samples. While binary class labels are described as an example, the training samples may also include multi-class labels in different embodiments.

The computing server 130 may adjust 670 one or more weights of the machine learning model 610 based on the objective function. The adjustment may be referred to as a back propagation. The adjustment of the weights may be conducted using gradient descent techniques such as stochastic gradient descent. Multiple rounds of training may be performed. Each round may include inputting 640 feature vectors to the machine learning model 610, determining 660 the value of the objective function in the current iteration, and adjusting 670 the weights of the machine learning model 610 using coordinate descent. Training may be completed until a stopping condition. A stopping condition may occur when the objective function has become sufficiently stable (e.g., the machine learning model has converged) or after a predetermined number of iterations (e.g., sufficient epochs) for a particular set of training samples. A trained model 610 may be used to predict the relationship between a potential common ancestor and a target individual.

In some embodiments, a validation set may be formed of additional training samples, other than those in the training. The computing server 130 applies the trained validation machine learning model 610 to the feature vectors of the validation set to quantify the accuracy of the machine learning model 610. Common metrics applied in accuracy measurement include: Precision ("P")=TP/(TP+FP) and Recall ("R")=TP/(TP+FN), where precision is how many the machine learning model 610 correctly predicted (TP or true positives) out of the total it predicted (TP+FP or false positives), and recall is how many the machine learning model 610 correctly predicted (TP) out of the total number of content items that did have the property in question (TP+FN or false negatives). The F score (F-score=2*PR/ (P+R)) unifies precision and recall into a single measure.

In some embodiments, deep learning techniques may also be used. Examples of deep learning machine learning models may include neural networks, including convolutional neural networks (CNN), recurrent neural networks (RNN) and long short-term memory networks (LSTM).

Figure 7:
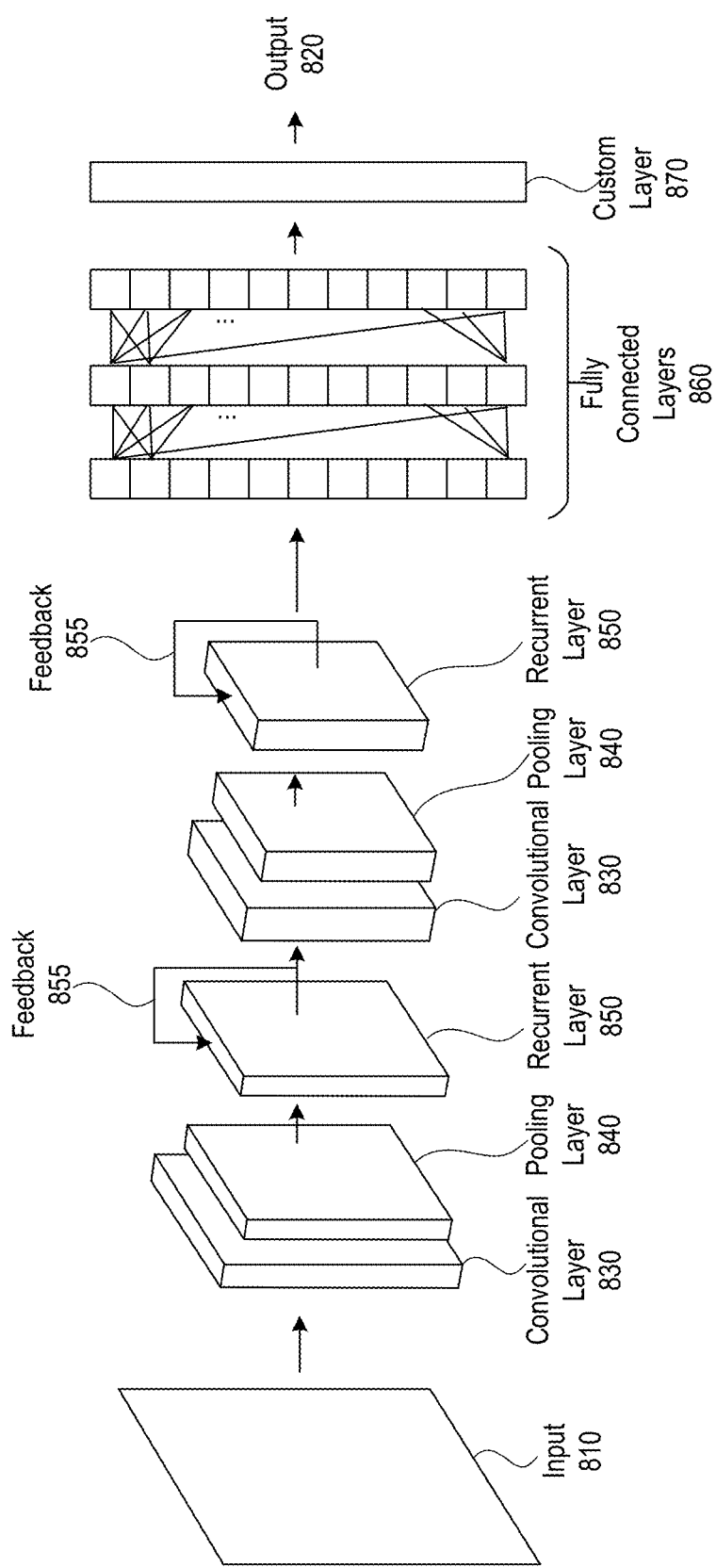
FIG. 7 is a conceptual diagram illustrating a structure of an example CNN, according to some embodiments.

Referring to FIG. 7, a structure of an example CNN is illustrated, according to an embodiment. The CNN 700 may be an example of a machine learning model 610. The CNN 700 may receive an input 710 and generate an output 720. The CNN 700 may include different kinds of layers, such as one or more convolutional layers 730, pooling layers 740, recurrent layers 750, full connected layers 760, and custom layers 770. A convolutional layer 730 convolves the input of the layer with one or more kernels to generate different types of data that are filtered by the kernels to generate feature maps. Each convolution result may be associated with an activation function. A convolutional layer 730 may be followed by a pooling layer 740 that selects the maximum value (max pooling) or average value (average pooling) from the portion of the input covered by the kernel size. The pooling layer 740 reduces the spatial size of the extracted features. In some embodiments, a pair comprising a convolutional layer 730 and a pooling layer 740 may be followed by a recurrent layer 750 that includes one or more feedback loops 755. The feedback loop 755 may be used to account for spatial relationships of the features in an image or temporal relationships of the objects in the image. The layers 730, 740, and 750 may be followed in multiple fully connected layers 760 that have nodes (represented by squares in FIG. 7) connected to each other. The fully connected layers 760 may be used for classification and object detection. In one embodiment, one or more custom layers 770 may also be presented for the generation of a specific format of output 720. For example, a custom layer 770 may be used for image segmentation for labeling pixels of an image input with different segment labels.

The order of layers and the number of layers of the CNN 700 in FIG. 7 is for example only. In various embodiments, a CNN 700 includes one or more convolutional layers 730 but may or may not include any pooling layer 740 or recurrent layer 750. If a pooling layer 740 is present, not all convolutional layers 730 are always followed by a pooling layer 740. A recurrent layer 750 may also be positioned differently at other locations of the CNN 700. For each convolutional layer 730, the sizes of kernels (e.g., 3×3, 5×5, 7×7, etc.) and the numbers of kernels allowed to be learned may be different from other convolutional layers 730. The kernels may also be one dimension, two dimensions, or multiple dimensions.

A machine learning model may include certain layers, nodes, kernels and/or coefficients. Training of a neural network, such as the CNN 700, may include forward propagation and backpropagation. Each layer in a neural network may include one or more nodes, which may be fully or partially connected to other nodes in adjacent layers. In forward propagation, the neural network performs the computation in the forward direction based on outputs of a preceding layer. The operation of a node may be defined by one or more functions. The functions that define the operation of a node may include various computation operations such as convolution of data with one or more kernels, pooling, recurrent loop in RNN, various gates in LSTM, etc. The functions may also include an activation function that adjusts the weight of the output of the node. Nodes in different layers may be associated with different functions.

Each of the functions in the neural network may be associated with different weights (e.g. weights and kernel coefficients) that are adjustable during training. In addition, some of the nodes in a neural network may also be associated with an activation function that decides the weight of the output of the node in forward propagation. Common activation functions may include step functions, linear functions, sigmoid functions, hyperbolic tangent functions (tanh), and rectified linear unit functions (ReLU). After an input is provided into the neural network and passes through a neural network in the forward direction, the results may be compared to the training labels or other values in the training set to determine the neural network's performance. The process of prediction may be repeated for other data in the training sets to compute the value of the objective function in a particular training round. In turn, the neural network performs backpropagation by using gradient descent such as stochastic gradient descent to adjust the coefficients in various functions to improve the value of the objective function.

Multiple rounds of forward propagation and backpropagation may be performed. Training may be completed when the objective function has become sufficiently stable (e.g., the machine learning model has converged) or after a predetermined number of rounds for a particular set of training samples. The trained machine learning model can be used as machine learning model 610.

Figure 8:
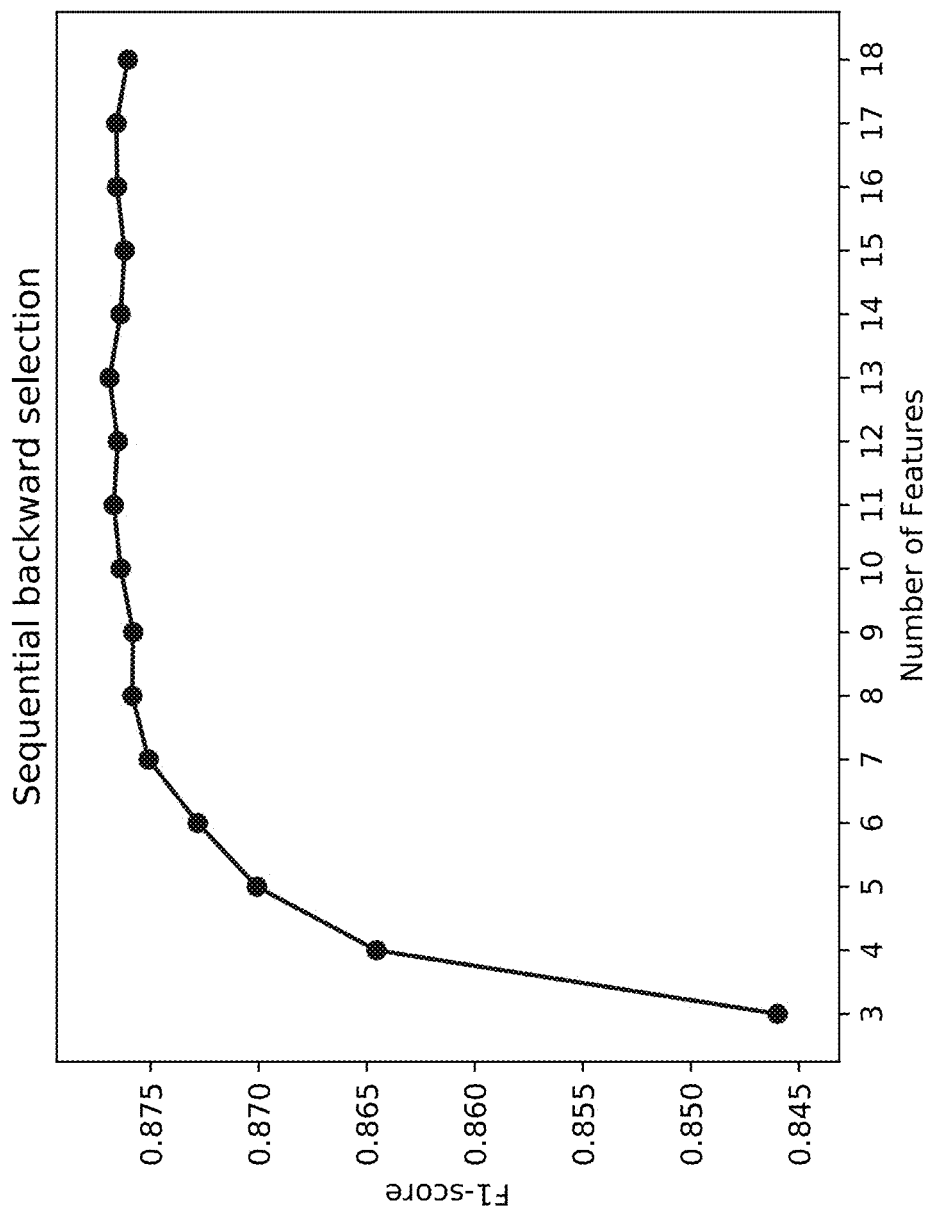
FIG. 8 is a chart illustrating the performance of a machine learning model versus the number of features used in training the model, in accordance with some embodiments.
Figure 9:
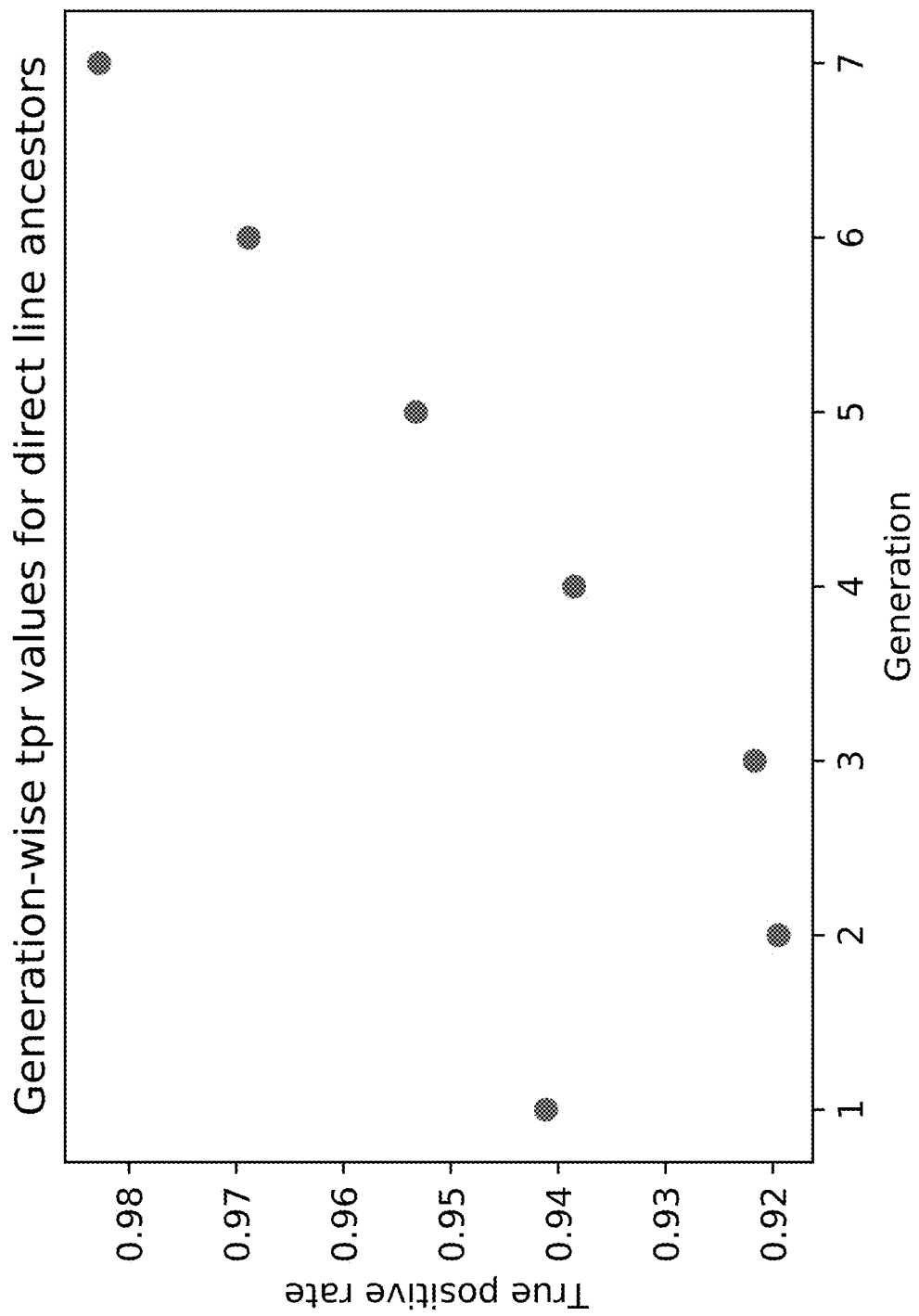
FIG. 9 is a chart illustrating the true positive rate of a machine learning model versus the number of generations between a target individual and a potential common ancestor.

FIG. 8 is a chart illustrating the performance of a machine learning model 610 versus the number of features used in training the model, in accordance with some embodiments. The features are those discussed in step 440 of process 400. FIG. 8 shows that a machine learning model 610 may achieve acceptable performance using three features and the performance starts to converge with seven or more features. The types of features that impact the performance the most may also be identified using sequential backward selection techniques. FIG. 9 is a chart illustrating the true positive rate of a machine learning model 610 versus the number of generations between a target individual and a potential common ancestor. The performance increases as the number of generations increases, as it has been surprisingly found that the existence of descendants who match with the target individual despite the larger age and generation gap between the target individual and the potential common ancestor is highly probative of direct-line ancestry.

ASSIGNING TARGET INDIVIDUAL TO A FAMILY TREE

Figure 10:
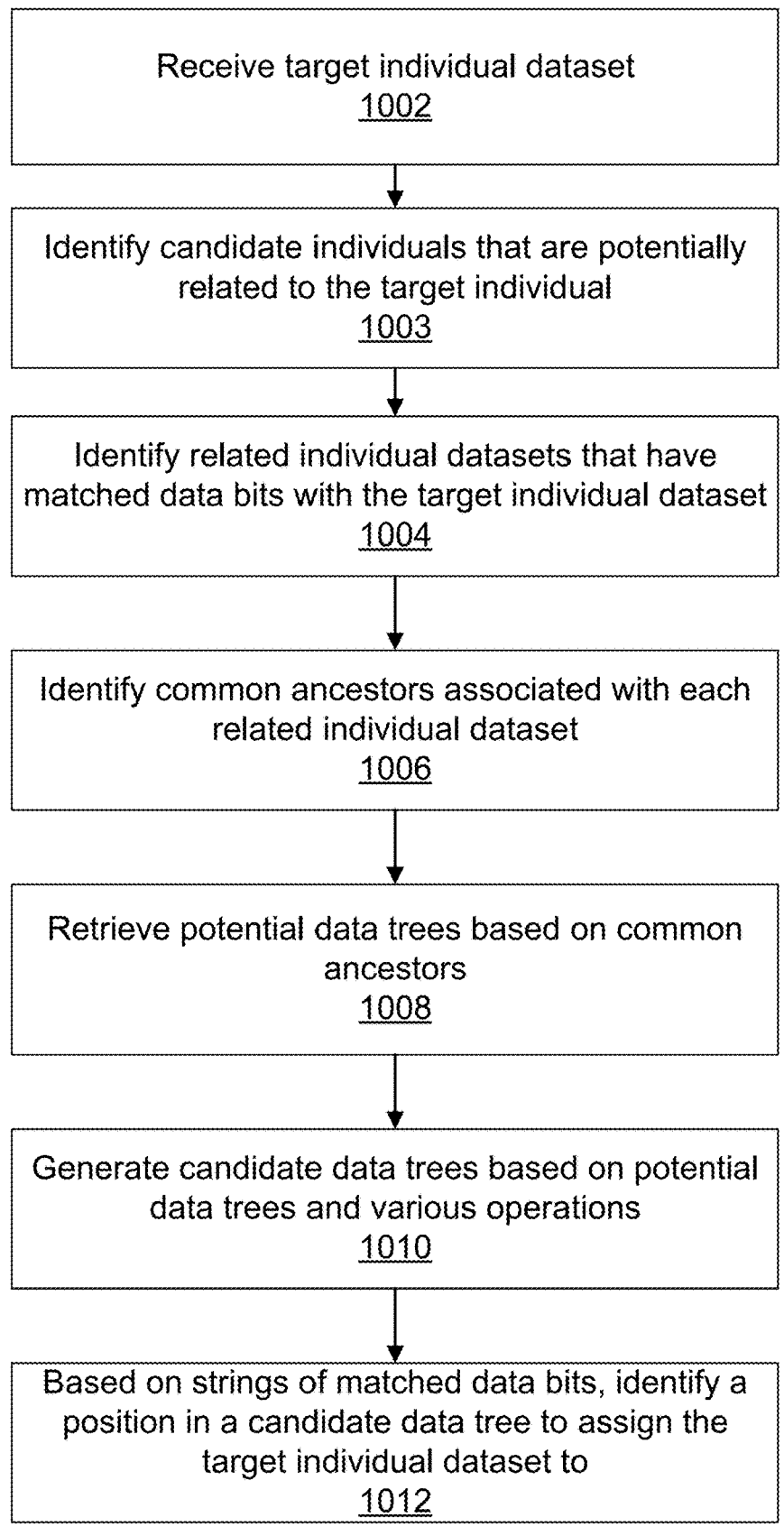
FIG. 10 is a flow chart illustrating an example process that includes various links a target individual to a family tree, in accordance with some embodiments.

FIG. 10 is a flow chart illustrating an example process that include various links a target individual to a family tree, in accordance with some embodiments. Linking the target individual to a family tree may include determining one or more estimated locations where the target individual should fit at the family tree based on the genetic and genealogical relationship between the target individual and the individuals in the family tree. Upon linking the target individual, the computing server 130 may assign metadata to the dataset of the target individual to serve as an indication that the target individual's dataset is linked to the family tree, which may take the form of a data tree in a database.

The computing server 130 may receive 1002 a dataset associated with the target individual. The computing server 130 may identify 1003 a plurality of individuals that are potentially related to the target individual. For example, the computing server 130 may identify individuals that have genetic data available in the database as candidate individual. A DNA tester may be a user who has completed a DNA test that extracts the user's DNA data through the genetic data extraction server 125. The extracted genetic data, which may include genotype or haplotype data, is stored in the genetic data store 205. Candidate individual datasets are genetic datasets corresponding to those candidate individuals. The candidate individuals are potentially related to the target individual subject to further analysis.

From the candidate individuals, the computing server 130 may identify 1004 one or more related individuals or matched individuals for the target individual based on shared IBD information between the target individual and potential matched individuals. The computing server 130 may identify a related individual dataset from the plurality of candidate individual datasets based on matched data bits such as shared genetic data bits. For example, the computing server 130 may identify a matched individual that has a certain amount of IBD segments shared with the target individual. With IBD estimation engine 225, the computing server 130 may determine the length of IBD segments shared by the target individual and a candidate individual. The computing server 130 may select one or more candidate individuals as potential matched individuals of the individuals based on one or more suitable selection criteria. For example, the criteria may be the shared IBD segments being higher than a threshold, the two individuals being closely related in an IBD community as determined by community assignment engine 230, or other suitable conditions. The matched individuals may be further filtered based on whether the matched individuals have family trees available in the database. A matched individual may be referred to as a related individual whose genetic dataset may be referred to as a related individual dataset.

For each identified matched individual, the computing server 130 may identify 1006 one or more common ancestors for the target individual and the identified matched individual. The common ancestors may be identified through one or more family trees that are related to the target individual and/or the matched individual. A family tree or a family tree may be represented as a data tree and a common ancestor may be represented as a parent node, which is a common parent node for both the related individual dataset and the target individual dataset. The common ancestor may be a DNA tester, a non-DNA tester but user of the computing server, or a historical person in a genealogical record.

In some cases, the computing server 130 may identify a potential common ancestor through a "big tree," which may be a large-scale network of individuals whose interrelationships are maintained and discovered by the computing server 130. The computing server 130 may construct a large-scale network by concatenating a large number of family trees of different users. Various users, whether having their genetic data stored in computing server 130 or not, may have constructed one or more family data by using genealogy data store 200 to link individuals, such as DNA testers, other users of computing servers 130 who have not completed a DNA test, or historical individuals whose records are found in one or more genealogical data records. Based on users' permission to share the information, the computing server 130 may generate a large-scale network of individuals that include DNA testers, other users who have not completed DNA tests, and historical individuals. The large-scale network may include a very large number of people (such as many users of the computing server 130 and many other historical individuals who have been included in one or more family trees of users). The computing server 130 may collect a large number of family trees and link the trees together by identifying one or more common individuals in two or more trees.

The computing server 130 may identify one or more potential common ancestors by using one or more family trees, such as using the large-scale network. For example, the computing server 130 may determine that the target individual and the matched individual are in fact connected in the large-scale network. The computing server 130 may identify one or more potential common ancestors who are in the path(s) connecting the target individual and the matched individual. Because one or more potential common ancestors may be identified through the large-scale network, those potential common ancestors may not be individuals who are listed in the target individual's genealogical profile, the matched individual's genealogical profile, or any of the two persons' family trees.

The computing server 130 may provide one or more matched individuals for a user (who is usually the target individual) to select through a user interface. Based on the selection of a matched individual, the computing server 130 may provide one or more suggestions of potential common ancestors to the target individual. The user has the option to select one of the potential common ancestors to further explore. The computing server 130 may receive the user's selection and may start to retrieve connections that form a path between the target individual and the matched individual through the selected potential common ancestor. To complete a full connection, the computing server 130 may first identify a connection who has a linkage that connects the target individual towards the selected potential common ancestor. The computing server 130 may identify a connection who has a linkage that connects the matched individual towards the selected potential common ancestor. After one or more connections are retrieved and established, the above steps may be repeated until the path between the target individual and the matched individual through the common ancestor is completed. Alternatively, or additionally, the computing server 130 may connect the first linkage and the second linkage with the selected potential common ancestor by adding one or more individuals to complete the connection. One example embodiment describing identification of common ancestors is described in U.S. Patent Application Publication No. 2020/0273542, entitled "Graphical Use Interface Displaying Relatedness Based on Shared DNA," published on Aug. 27, 2020, which is incorporated by reference in its entirety for all purposes.

In some cases, the number of identified common ancestors may be enormous and hard to manipulate, the identified common ancestors may be pruned and filtered to the ones that are the most likely to be common ancestors that connect the target individual with the matched individuals. Steps for pruning common ancestors are discussed in detail in FIG. 11. With the identified common ancestors, the computing server 130 may retrieve 1108 family trees associated with the identified closest common ancestors. For example, the computing server 130 may retrieve data trees that the identified parent nodes belong to. The data trees contain inter-relationships among datasets of the individuals in the data trees. These family trees may be referred to as potential family trees that the target individual may belong to. The potential family trees may be identified through the large-scale network, "big tree," by retrieving all descendants of a closest common ancestor with the closest common ancestor as the root of the family tree. Along with the potential family trees, the computing server 130 also retrieves genetic information of the individuals who are in the potential family trees and have genetic information available. With the retrieved potential family trees and genetic information for individuals in the potential family trees, the computing server 130 may determine a position of the target individual to assign in the potential family trees.

To assign the target individual to a position in a potential family tree, the computing server 130 may perform various operations and generate 1010 candidate data trees. In this context, a potential family tree may refer to an existing family tree already in the computing server 130 while a candidate data tree may refer to one of the possible trees to place the target individual in an existing family tree. The candidate data trees may be generated from different operations such as replacing, splitting, and extending. The various operations may include replacing, extending, or splitting one or more nodes in the potential family tree. For example, given a family tree and a target individual, one possible way to fit the target individual in the family tree is to replace an existing individual that is not a matched individual in the family tree. A candidate data tree may be generated by replacing an individual in the family tree with the target individual. The extending operation extends a leaf node in the family tree by adding the target individual as a decedent of the leaf node. Similarly, the splitting operation may split a parent node in the family tree by adding the target individual as one of the descendants of the parent node. Each operation may be performed on each applicable node in the family tree, thereby resulting in a plurality of candidate data trees. Additionally, a candidate data tree may also be generated by assuming the target individual is not related to a common ancestor in the tree, which is discussed in FIG. 12 in accordance with step 1209. Details of generating candidate data trees by using these operations is discussed in FIG. 12 and the operations are illustrated in FIGS. 13A-13D.

Since the candidate data trees are generated based on existing family trees that include the common ancestors identified from step 1006 and the related individuals identified from step 1004, each candidate data tree generated from the operations mentioned above contains at least one of the identified matched individuals from step 1004. As such, based on the matched DNA information between the target individual and the matched individuals, the computing server 130 may calculate a composite likelihood for each candidate data tree and identify one or more candidate data trees that are likely to be the family tree to which the target individual belongs. In some embodiment, the most likely candidate data tree is also identified. In turn, the computing server 130 may identify 1012 a position in the data tree based on string matched data bits (e.g. IBD segments, data bits in genetic datasets) and number of the matched strings (e.g. IBD spectrum) of the target individual dataset and the datasets of matched individuals in the data tree. The candidate tree also contains the target individual's position information in the family tree, which indicates the relationship between the target individual and individuals in the family tree. As a result, an estimated family tree and a position in the family tree is determined for the target individual. Detail regarding determination of composite likelihood is discussed in FIG. 12.

To illustrate and summarize the steps performed in FIG. 10 with a non-limiting example, the computing server 130 may identify a number of matched individuals (e.g. 200 matched individuals) for a target individual where the identified matched individuals may be individuals who share top amounts of IBD with the target individual. For each of the 200 matched individuals, a number of potential common ancestors (e.g. 255 common ancestors for each matched individual) may be identified. The total number of identified common ancestor is 200×255, which may be pruned by steps described in FIG. 11. The pruned common ancestors may be referred to as the closest common ancestors and a family tree associated with each closest common ancestor may be retrieved. For each retrieved family tree, operations such as replacing, extending, and splitting may be performed on each applicable node in the family tree and a group of candidate trees are generated. Finally, for each candidate data tree, a composite likelihood may be determined based on matched DNA information and a family tree and a position in the family tree may be identified for the target individual.

Figure 11:
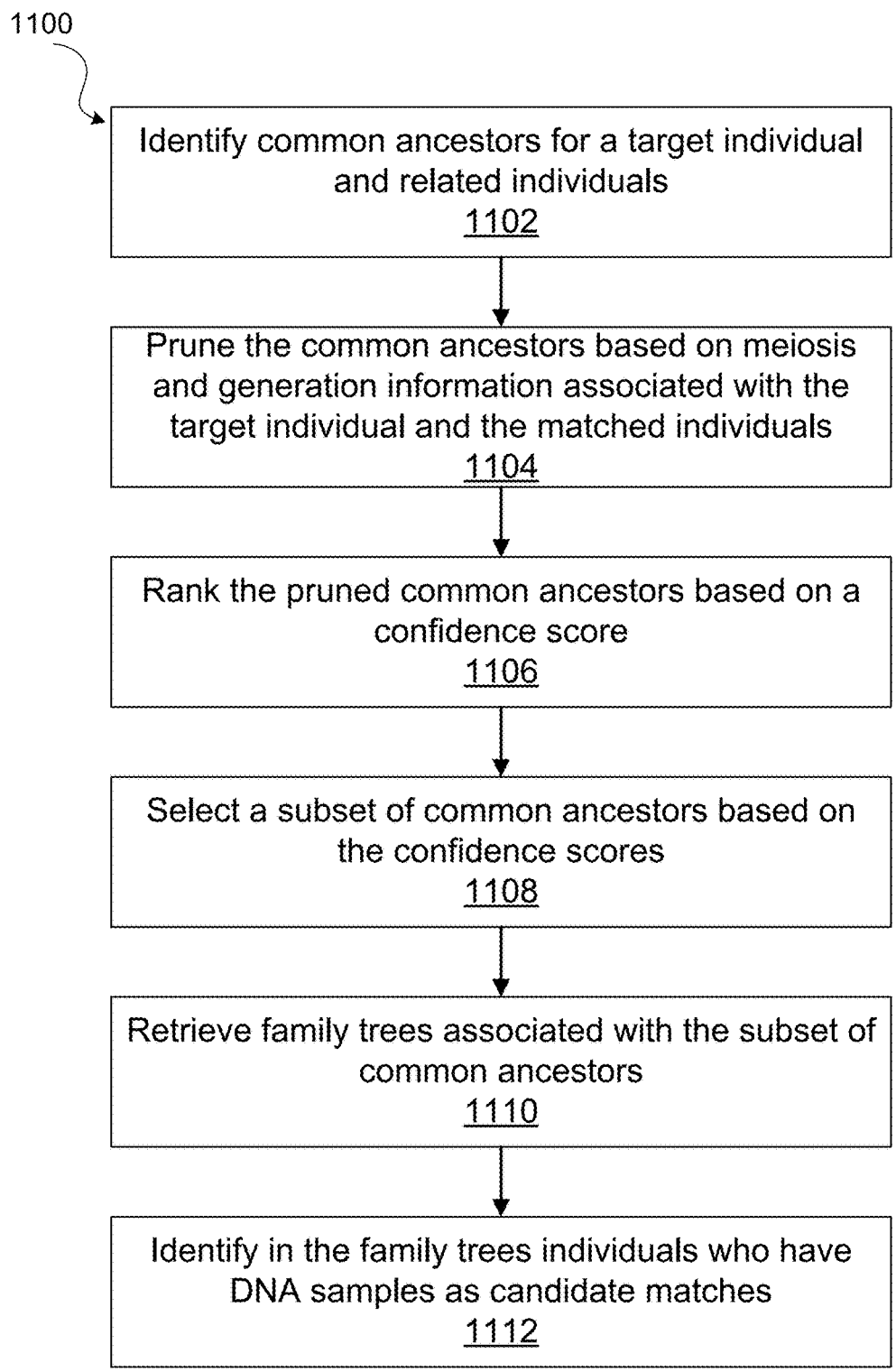
FIG. 11 is a flowchart illustrating an embodiment of a process for identifying potential data trees for a target individual dataset.

FIG. 11 is a flowchart illustrating an embodiment of a process for identifying potential data trees for a target individual dataset. The steps described in FIG. 11 correspond to and expand upon steps 1006 and 1008 in FIG. 10.

The computing server 130 may identify 1102 common ancestors associated with each matched individual. The number of common ancestors could be large. The common ancestors may be represented by candidate parent nodes in one or more data tree. The computing server 130 may prune and rank the large number of common ancestors. The common ancestors may be pruned 1104 based on meiosis and generation information associated with the target individual and the matched individuals. Meiosis represents a degree of relatedness of two individuals and is calculated based on the amount of IBD between the two individuals. Through meiosis, a relationship between two individuals may be estimated based on the amount of IBD shared between the pair of individuals. Meiosis may be characterized as the number of reproductive events separating two individuals, and as a result, meiosis is an integer greater than or equal to zero. For example, meiosis between a parent and child is one, because they are separated by one reproductive event. In another example, the meiosis between two full siblings is two, because two meiosis separate two full siblings through the path: sibling 1, parent, sibling 2. For more distant relationship or pairs that include more common ancestors, the meiosis may be calculated in any suitable ways such as based on the detailed framework set forth below in the Section entitled "Calculating M."

A generation value may refer to the number of generations between the common ancestor and the matched individual determined from the pedigree to which both the matched individual and the common ancestor belong. With meiosis information combined with generation value, a portion of the common ancestors may be eliminated. For example, a pair of third cousins may be estimated to have a meiosis of 7 based on IBD, which indicates that they share a most recent common ancestor that is a great-great-grandparent. Determining from pedigrees, third cousins who share a great-great-grandparent in common would have a number of generation value greater than or equal to four. Therefore, if the generation value between the matched individual and the common ancestor is 2, the respective common ancestor may be eliminated. As such, the computing server 130 determines a possible range for a generation value between the related individual and the parent node (e.g. common ancestor) based on a meiosis between the target individual and the related individual (e.g. matched individual). As illustrated in the example above, if the actual generation value (e.g. 2 in the example) is out of the range (e.g. greater than or equal to 12 in the example), the common ancestor is unlikely to be a common ancestor or parent node to both the target individual and the matched individual and the respective common ancestor may be eliminated.

The computing server may also rank 1106 the candidate common ancestors (e.g., the remaining common ancestors after pruning) based on a confidence score associated with each candidate common ancestor which is represented by a candidate parent node to the target individual and the matched individual. A confidence score is determined based on meiosis and generation information. In one embodiment, a confidence score may be calculated as 1/(meiosis*generation) for meiosis greater than 2. A confidence score may be determined based on other equations or relationships involving meiosis and generation. A confidence score that is closer to one indicates a closer relationship between the target individual and the matched individual and therefore represents a higher level of confidence associated with the common ancestor. For example, for a target individual as a child and a matched individual as a parent, the pair of parent/child has a meiosis of 1 and a generation value of 1. The confidence score for the common ancestor, which is also the parent, is 1/(1*1)=1, which indicates that the parent is extremely likely to be a true common ancestor. In another example, a meiosis of 2 between a target individual and a matched individual may indicate an immediate family relationship such as siblings, which also leads to a high confidence score. For meiosis values greater than 2, the confidence score is calculated by 1/(meiosis*generation). For example, if the meiosis between a target individual and a matched individual is 7 and the generation value between the matched individual and the common ancestor is 11, then the confidence score is calculated as 1/(7*4)=0.0357.

As such, a confidence score may be calculated for each common ancestor based on meiosis and generation information. The computing server 130 may select a certain number of common ancestors based on the confidence scores. In one embodiment, a certain percentage or a certain number of the highest ranked common ancestors may be selected.

The computing server 130 may retrieve 1110 pedigrees associated with the selected closest common ancestors. The pedigrees may be identified through the large-scale network, "big tree," by retrieving all descendants of a closest common ancestor with the closest common ancestor as the root of the pedigree.

The tree identification engine 260 may scan through the individuals in the retrieved pedigrees and identify 1111 individuals who have DNA samples available as candidate matches for the target individual. The tree identification engine 260 may analyze and retrieve information associated with the candidate matches such as genetic information, IBD, genealogy information or any information available. With the retrieved pedigree information and the candidate matches information, the computing server 130 may determine a position of the target individual in the pedigrees.

Figure 12:
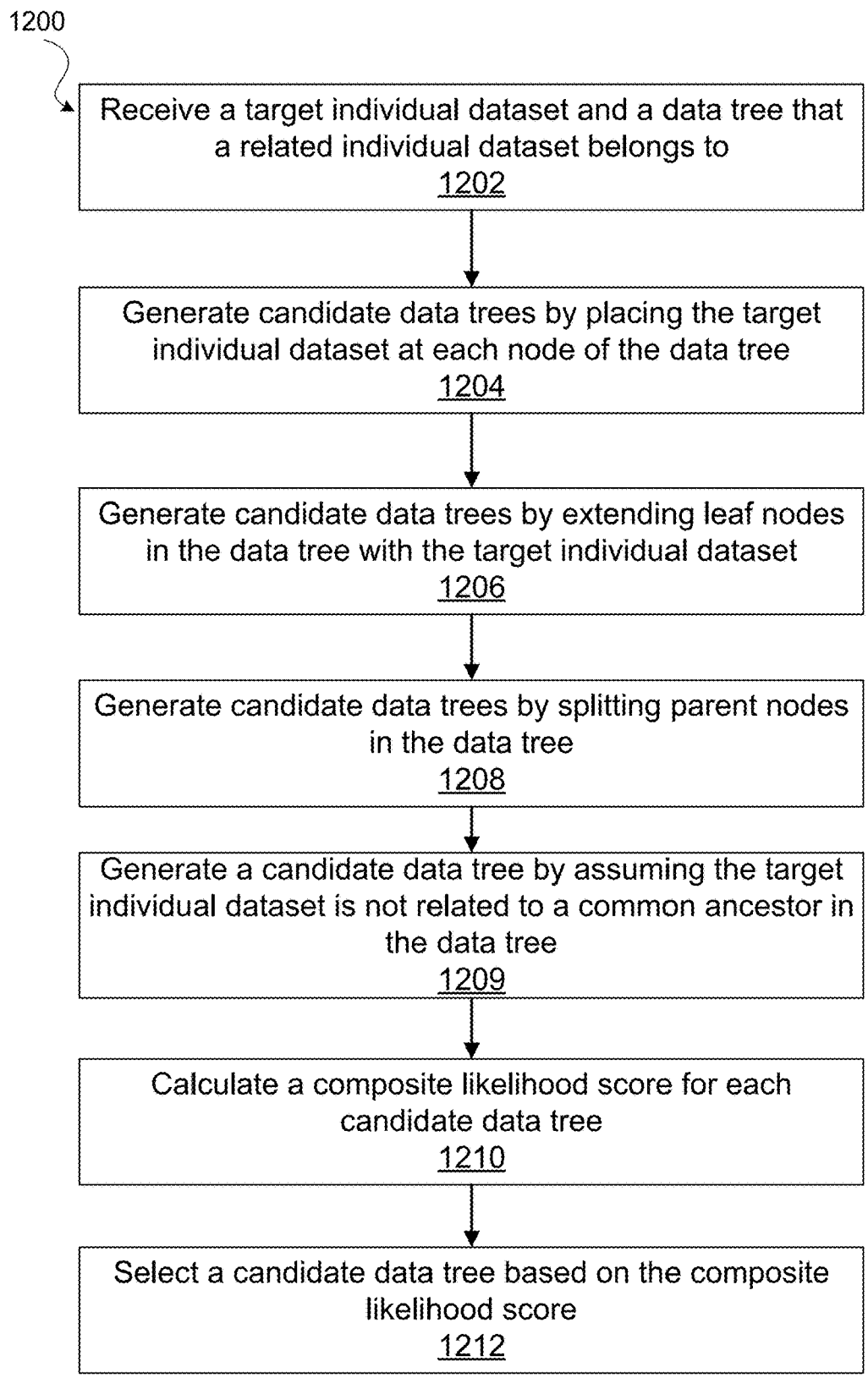
FIG. 12 is a flowchart illustrating an embodiment of a process for assigning a target individual data set to a position in a data tree.

FIG. 12 is a flowchart illustrating an embodiment of a process for assigning a target individual data set to a position in a data tree. The process may be performed repetitively on each pedigree and produce a group of candidate data trees with each candidate data tree representing a possible way indicating how to place the target individual in a pedigree. With information associated with the target individual, a potential pedigree, and candidate matches in the tree, a position of the target individual in the pedigree may be determined.

The determination process starts with receiving 1202 data associated with a target individual and a potential pedigree along with candidate matches in the tree. Then various operations such as steps 1204-1208 are performed on the potential pedigree, which may be referred to as a data tree. The computing server 130 may generate 1204 candidate data trees by placing the target individual dataset at each node of the data tree, generate 1206 candidate data trees by extending leaf nodes in the data tree with the target individual dataset, generate 1208 candidate data trees by splitting parent nodes in the data tree, and generate 1209 a candidate data tree by assuming that the target individual is not related to a common ancestor in the potential pedigree. A candidate data tree with a candidate position to place the target individual may be generated through one or more of the following operations. For example, the computing server 130 may assign the target individual to an existing node in the data tree as the candidate position with the target individual replacing the existing node. This operation is further discussed in FIG. 13B. The computing server 130 may add a child node that descends from a leaf node in the data tree as the candidate position for the target individual dataset. This operation is further discussed in FIG. 13C. The computing server 130 may also add a child node that descends from an inner node in the data tree, with the child node in a new branch descending from the inner node and the child node is the candidate position for the target individual dataset. This operation is further discussed in FIG. 13D. Based on the generated candidate data trees, the computing server 130 may calculate 1210 a composite likelihood score for each candidate data tree and select 1212 a candidate data tree as an estimated pedigree for the target individual based on the composite likelihood score. Each operation 1204-1208 is illustrated in detail in accordance to FIGS. 13A-13D, which are discussed in further detail.

Figure 13A:
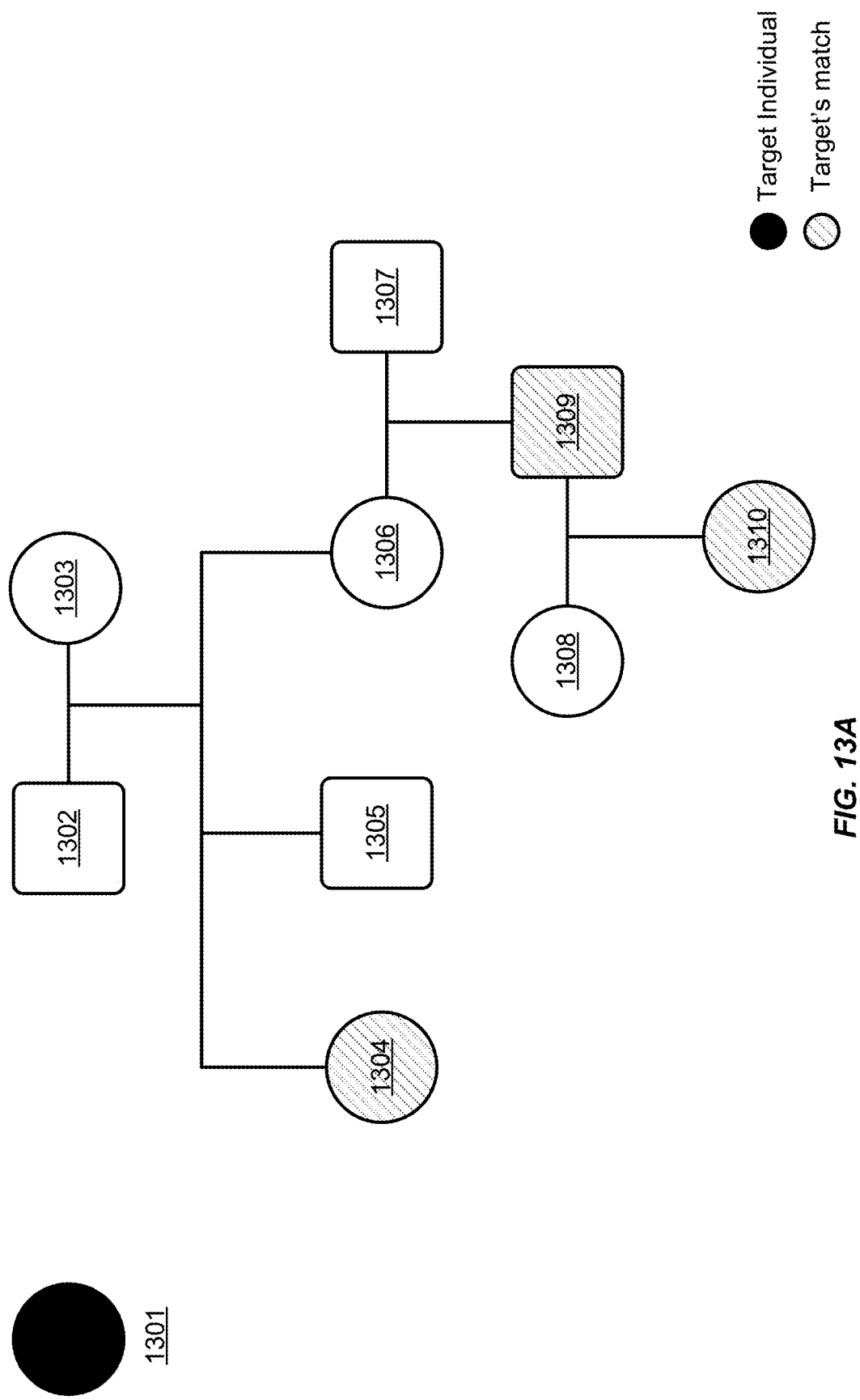
FIGS. 13A-13D illustrate various operations for identifying a position for a target individual in a data tree, in accordance with one embodiment.

FIGS. 13A-13D illustrate various operations for identifying a position for a target individual in a data tree, in accordance with one embodiment. FIG. 13A illustrates a pedigree and a target individual 1301 to be placed in the pedigree. In the pedigree, individuals 1304, 1309 and 1310 are candidate matches of the target individual 1301.

Figure 13B:
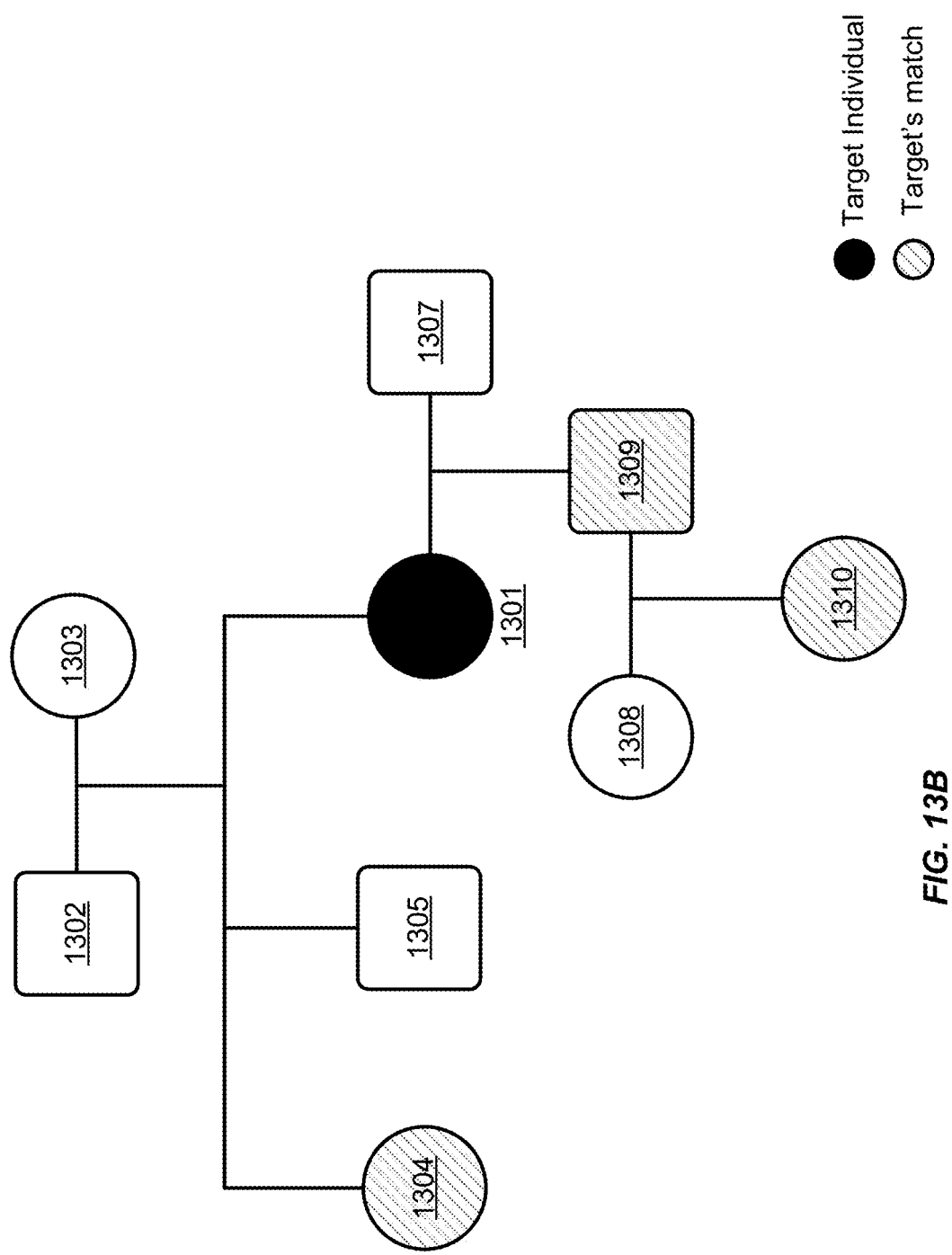

FIG. 13B illustrates an operation that replaces an existing individual in the pedigree that is not the target individual's candidate match. This operation may be an example of operations performed in step 1304 in FIG. 13. For example, as illustrated in FIG. 13B, the target individual 1301 replaces the position of individual 1306 who was originally in the pedigree illustrated in FIG. 13A. The replacing operation may be conducted on each node in the pedigree that is not a candidate match to the target individual 1301. In other words, replacing operation on each node may result in a candidate pedigree. For example, the pedigree illustrated in FIG. 13B is one of many possible candidate pedigrees due to replacing operation. Another pedigree may be produced by replacing individual 1308 with the target individual 1301.

Figure 13C:
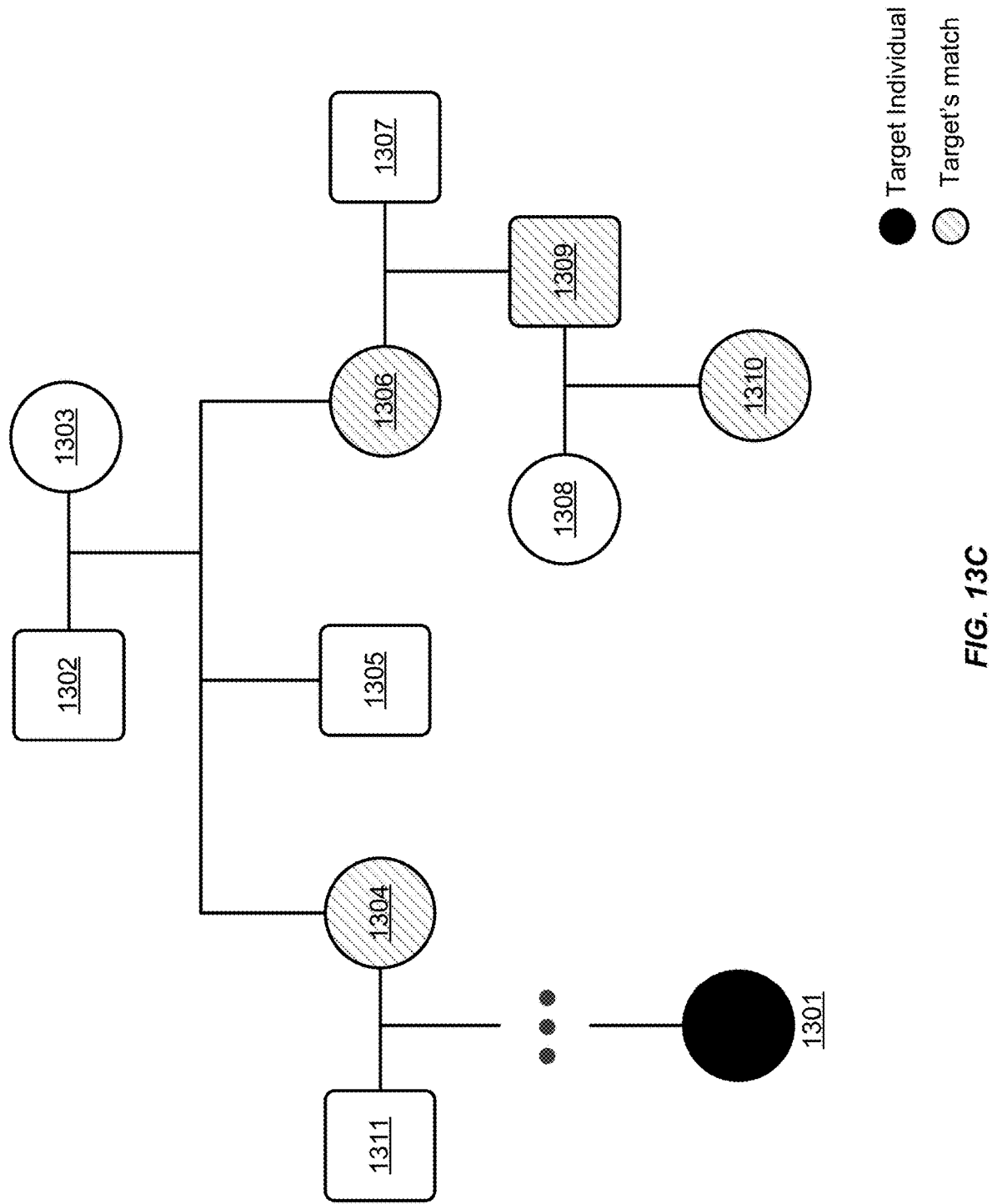

FIG. 13C illustrates an operation that extends a leaf node of the pedigree with the target individual 1301, which corresponds to step 1306 in FIG. 13. As illustrated in FIG. 13C, the target individual 1301 may be a descendant of individual 1304. The target individual 1301 may be a descendant one generation away from individual 1304 or may be any number of generations away. Each different possible way to place the target individual in the pedigree may produce a candidate tree. For example, the target individual may be places one generation apart from individual 1304 and results in a first candidate pedigree. The target individual may be two generations apart from individual 1304 and results in a second candidate pedigree. In another embodiment, the target individual 1301 may be descendant of individual 1310 and therefore additional candidate pedigrees may be further generated.

Figure 13D:
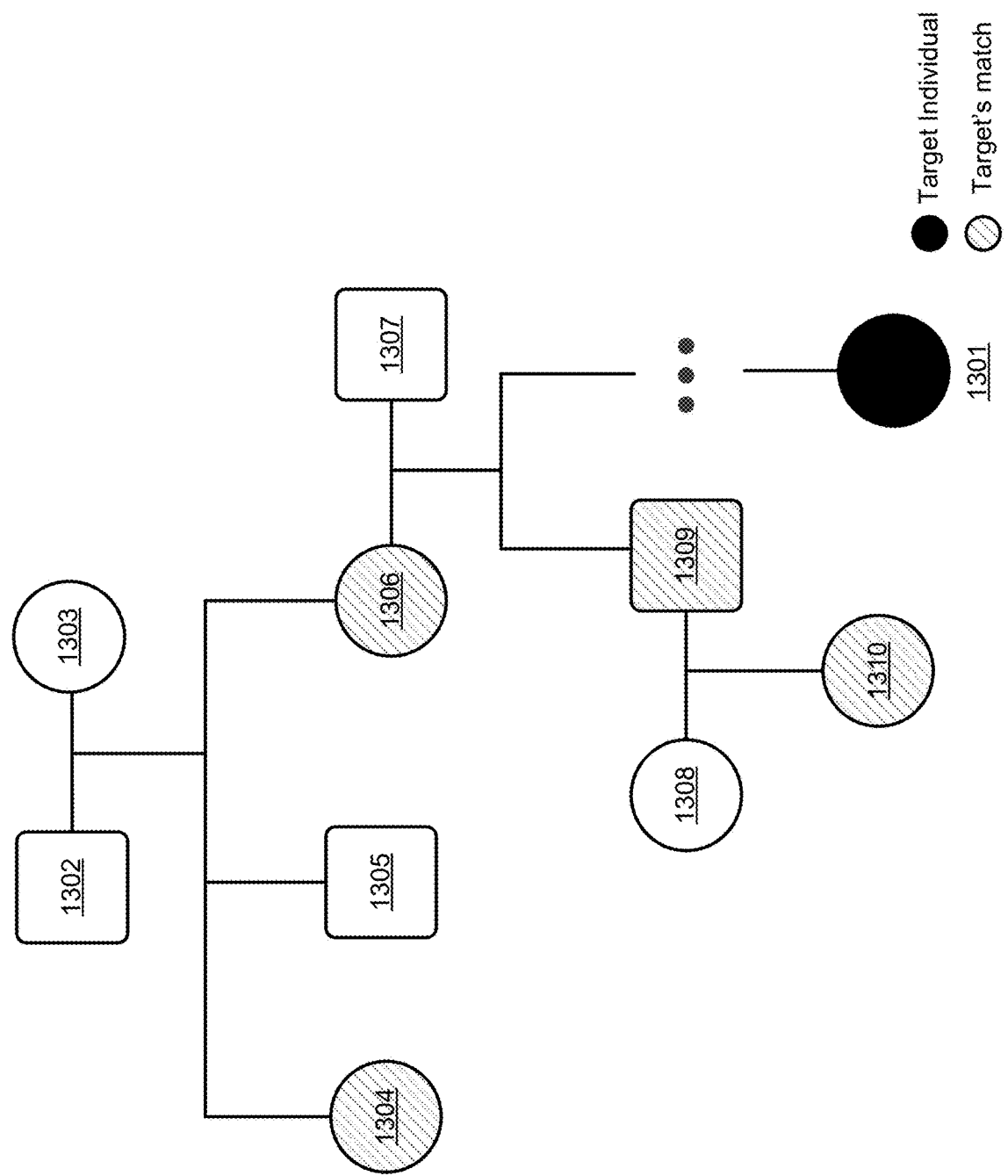

FIG. 13D illustrates an operation that splits a parent node of the pedigree by adding the target individual as a descendant of the parent node, which corresponds to step 1208 in FIG. 12. As illustrated in FIG. 13D, individuals 1306 and 1307 have a descendant 1309 as illustrated in the original pedigree in FIG. 13A. The target individual may be another descendant of individuals 1306 and 1307 in a branch that is parallel to the existing branch that individual 1309 belongs to. For example, in FIG. 13D, target individual 1301 is placed in the branch that is parallel to individual 1309. The target individual may be a descendant that is a number of generations away from an immediate child of individuals 1306 and 1307 or the target individual 1301 may be an immediate child of individuals 1306 and 1307 (i.e. a sibling of individual 1309). Similar to the extending operation, each possible position of target individual 1301 may generate a candidate pedigree. For example, if the target individual 1301 is one generation away from individuals 1306 and 1307, a candidate pedigree may be generated. If the target individual is two generations apart from the individuals 1306 and 1307, another candidate pedigree may be generated. In another possible situation where the target individual 1301 is a descendant of individuals 1302 and 1303, additional possible candidate pedigrees may be generated.

For operations illustrated in FIGS. 13B-13D, optimization may be performed to eliminate positions that are unlikely to assign the target individual to. In one embodiment, optimization may be performed based on metadata associated with the target individual and individuals in the pedigree. Some examples of metadata include but not limited to sex, age, date of birth, date of death or any demographic information. For example, for a replacing operation illustrated in FIG. 13A, if the target individual 1301 is a female, then it is unlikely for the target individual to be placed at nodes that are known to be males such as nodes 1302, 1305, 1307 and 1308. To illustrate with another example, for an extending operation illustrated in FIG. 13C, the target individual is unlikely to be a descendant of an individual who was born after the target individual. As a result, through optimization based on metadata, a number of potential candidate trees may be eliminated and therefore computational complexity is reduced.

Referring back to FIG. 12, a candidate data tree may also be generated 1209 by assuming that the target individual dataset is not related to a common ancestor in the pedigree. If no recent common ancestor information is known, a probability may be determined by integrating over all possible generations at which the two individuals could share a common ancestor.

Continuing with FIG. 12, through various operations such as steps 1204-1209, candidate trees are generated where each candidate tree represents a possible way to place the target individual in potential pedigrees. For each candidate tree, a composite likelihood score may be calculated 1210 based on genetic data and genealogical data associated with the target individual and candidate matches in the candidate tree. Calculation with regard to composite likelihood is discussed in further detail below.

In one embodiment, the likelihood of the relationship between two individuals i and j is calculated based on observed IBD $L_{ij}$ such as length or number of segments of IBD between individuals i and j. The relationship between individuals i and j may be referred to as $g=(g_i, g_j)$. Suppose the pedigree includes M candidate matches, the full likelihood of the IBD sharing may be approximated to be a product of pairwise sharing between the target individual and all other candidates in the pedigree, that is, M pairs of individuals in the network. Therefore, it is necessary to obtain a way of calculating the likelihood of the relationship $g_i$, $g_j$ between two individuals i, j for observed IBD $L_{ij}$. For ease of notation, the likelihood is expressed as $L(g)=P(L_{ij}|g)$, which may be used as a building block for the composite likelihood.

The first step is to model the length of an IBD segment shared by two related individuals given that the two individuals find a most recent common ancestor (MRCA) at g generations in the past. For a pair of individuals i and j, assume that they do not have more than a single individual or couple that is a recent common ancestor (CA) between (i.e. no inbreeding). Suppose that these individuals find a common ancestor at $g_i$, $g_j$ generations back from their own generation, respectively. With the exception of full siblings (with two IBD sharing segments which violates assumptions), at a given site in the genome, the density of IBD length l (in centimorgans) is given by:

$$p(l \mid g_i, g_j) = \begin{cases} 2^{-g_i-g_j+1+\delta(i,j)} \left(\dfrac{g_i+g_j}{100}\right)^2 l e^{-\frac{g_i+g_j}{100}l}, & \text{if } l > 0 \\ 1 - 2^{-g_i-g_j+1+\delta(i,j)}, & \text{if } l = 0 \end{cases}$$

where, $$\delta(i, j) = \begin{cases} 0, & \text{if } CA(i, j) \text{ is an individual} \\ 1, & \text{if } CA(i, j) \text{ is a couple} \end{cases}$$

Therefore, $\delta(i, j)=0$ is equivalent to one of the two cases: 1) i and j are half-relatives, or 2) i is an ancestor of j or vise-versa. For example, if i is the parent of j, then $\delta(i, j)=0$.

Note that the segment length is conditional on the length being nonzero (i.e. $p(l|l>0, g_i, g_j)$) and has an Erlang-2 distribution. That is, it takes the distribution of the sum of two exponential random variables, each corresponding to the closest recombination breakpoint to the site of interest that has occurred throughout all meiosis between i and j. Specifically, the distribution is equivalent to the distribution of $X_1+X_2$, where $X_1$ and $X_2$ are independent identical distribution (iid) of $$\text{Exp}\left(\frac{g_i+g_j}{100}\right),$$

which may be considered as the distribution of the sum of the minimums of two iid vectors of iid Exp(100) variables with one vector of length $g_i$ and the other vector of length $g_j$. Intuitively, the greater the value of g, the more likely the IBD is split into a smaller piece. US Patent Application Publication No. US2021/0216556A1, entitled "Linking Individual Datasets to a Database," published on Jul. 15, 2021, is incorporated herein for all purposes.

The second step is to model the spectrum of IBD segments shared by two related individuals. For some observed spectrum of n IBD segments $L=(L_1, L_2, \ldots, L_n)$ shared between i and j, it is assumed that the likelihood for $g=(g_i, g_j)$ is:

$$L(g) = \begin{cases} P(N=n \mid g) \prod_{k=1}^{n} q(l_k \mid g), & \text{if } n > 0 \\ P(N=0 \mid g), & \text{if } n = 0 \end{cases}$$

It is presumed that given the number of IBD segments, the lengths are conditionally independent of one another and are identically distributed.

Note that the distribution q in the product is a different distribution than the distribution p discussed above. The distribution q may be perceived as the length-normalized distribution of segments, that is, conditioning on any arbitrary N=n, q is the distribution of how frequent a single segment of length l is among those n segments of varying length. The distribution of q is derived as:

$$q(l \mid g) = \frac{p(l \mid g)}{l} / \int_0^{+\infty} \frac{p(l \mid g)}{l} dl = \frac{g_i + g_j}{100} e^{-\frac{g_i + g_j}{100} l}$$

As a result from the modeling, the number of segments and the total IBD length are sufficient to infer g, that is:

$$L(g) = P(N = n \mid g) \prod_{k=1}^{n} q(l_k \mid g) = P(N = n \mid g) \left(\frac{g_i + g_j}{100}\right)^n e^{-\frac{g_i + g_j}{100} \Sigma_k l_k}$$

This proves that for most pairwise relationships, the number and the total length of the IBD segments are sufficient to infer the underlying relationship g.

In practice, it is useful to just examine IBD segments that are thresholded below by a certain u>0. In such case, the distribution of q is derived as:

$$q_u(l \mid g) = \frac{p(l \mid g)}{l} / \int_u^{+\infty} \frac{p(l \mid g)}{l} dl$$

For l>u, the distribution of $q_u$ is proportional to the original q. For example, a threshold u=5 is used in the analysis.

The number of IBD segments (thresholded by u) is modeled as a Poisson random variable with rate parameter λ, with $$\lambda = \frac{\gamma}{100} 2^{-g+1+\delta(i,j)} g e^{-\frac{u}{100}g},$$

where γ is genome length in cM.

If no recent common ancestor information is known, the approach is to integrate over all possible generations at which the two individuals could share a CA, and the probability of waiting t generations to find a common ancestor is modeled as a geometric distribution with success rate $$\frac{1}{N_e}$$

where $N_e$ is the effective population size. The segment length distribution is modeled as $$p_{bkgd}(l) = \frac{2N_e(50 + N_e \times \mu)^2}{(50 + l \times N_e)^3}.$$

The number of IBD segments as a Poisson random variable with rate parameter $$\lambda_{bkgd} = \frac{\gamma \times 50 \times N_e}{(50 + N_e \times \mu)^2}.$$

To compute the composite likelihood for a pedigree based on observed IBD segments, consider the individuals in a pedigree of with genetic data and assume the number of such individuals is M. Each pair of individuals i and j in the pedigree has $g_i$ and $g_j$ number of generations to the most recent common ancestor (CA). For ease of notation, g=($g_i$, $g_j$). Let $l^{(i,j)}$ denote the observed spectrum of IBD segments between the pair of individuals i and j. For the case when there is no IBD sharing, denote $l^{(i,j)}=\{\emptyset\}$. Let the number of segments $n_{ij}=|l^{(i,j)}|$. The composite likelihood of $g:=(g_{ij})_{i \neq j}$ is given by:

$$CL(g) = \prod_{i \neq j} P(l^{(i,j)} \mid g_{ij})^{\frac{1}{M-1}} = \prod_{i \neq j} \left[ P(N = n_{ij} \mid g_{ij}) \prod_{k=1}^{n_{ij}} q(l_k^{(ij)} \mid g_{ij}) \right]^{\frac{1}{M-1}}$$

Intuitively, the equation above determines a likelihood for each pair of individuals i and j in the pedigree and generates a composite likelihood by multiplying the likelihood for each pair of individuals. The likelihood for each pair of individuals indicates a probability that individuals i and j have $g_i$ and $g_j$ generations away from the common ancestor respectively based on observed IBD segments (i.e. matched DNA data bits). The composite likelihood is determined based on a product of the likelihood for each pair of individuals in the candidate data tree.

Therefore, based on a composite likelihood for each candidate pedigree, it is possible to detect if an individual belongs to a pedigree and where the individual may be positioned in the pedigree based on genetic information. For each operation illustrated in steps 1206-1210 in FIG. 12, candidate trees may be generated, and a composite likelihood may be calculated for each candidate tree. As such, based on the composite likelihood, the computing server 130 may select a candidate tree with a top-ranking composite likelihood.

EXAMPLE APPLICATION ON SIMULATED DATA

Figure 14A:
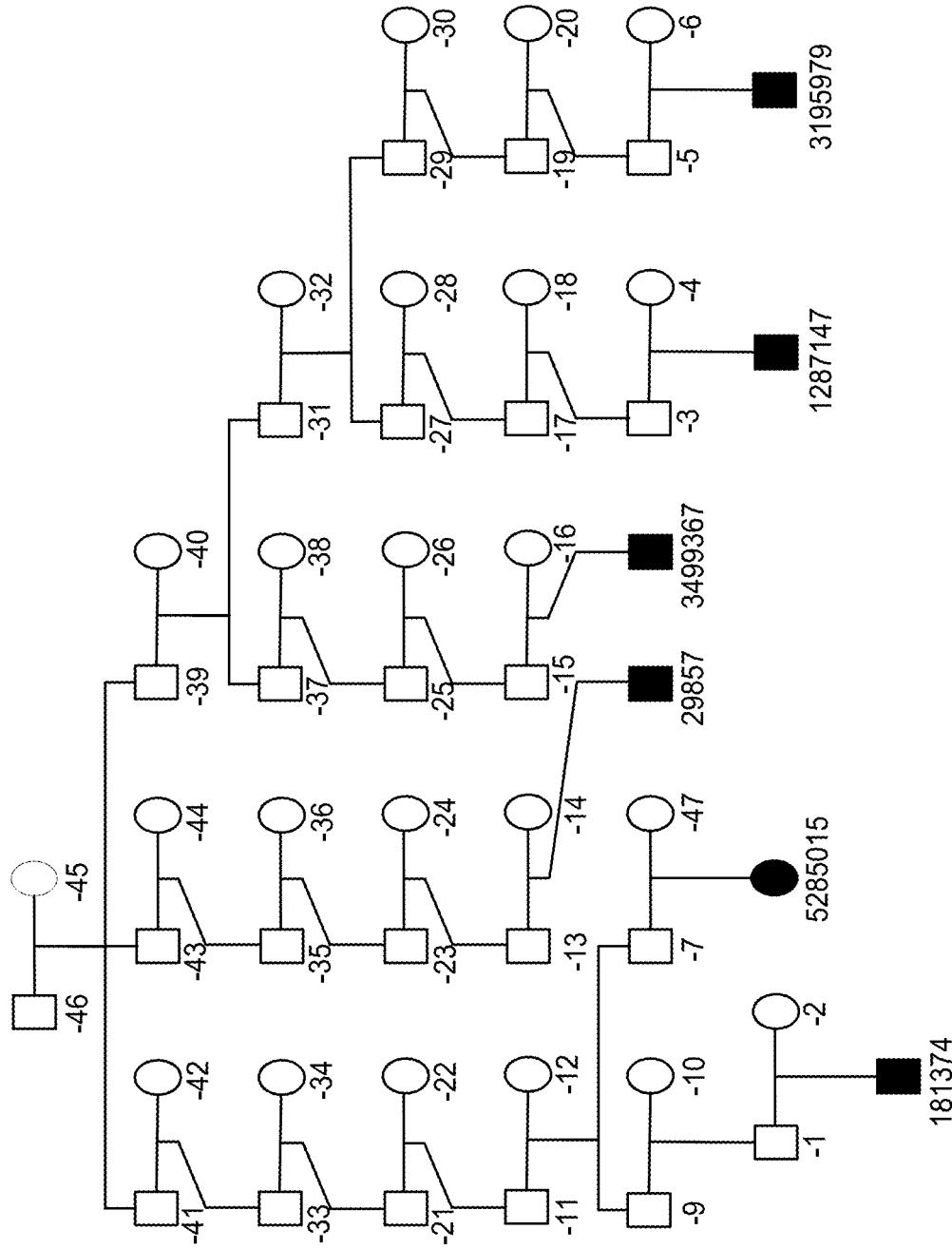
FIG. 14A illustrates one example of the true family tree that a target individual belongs to and FIG. 14B illustrates the two family trees with top log likelihood identified by the process.
Figure 14B:
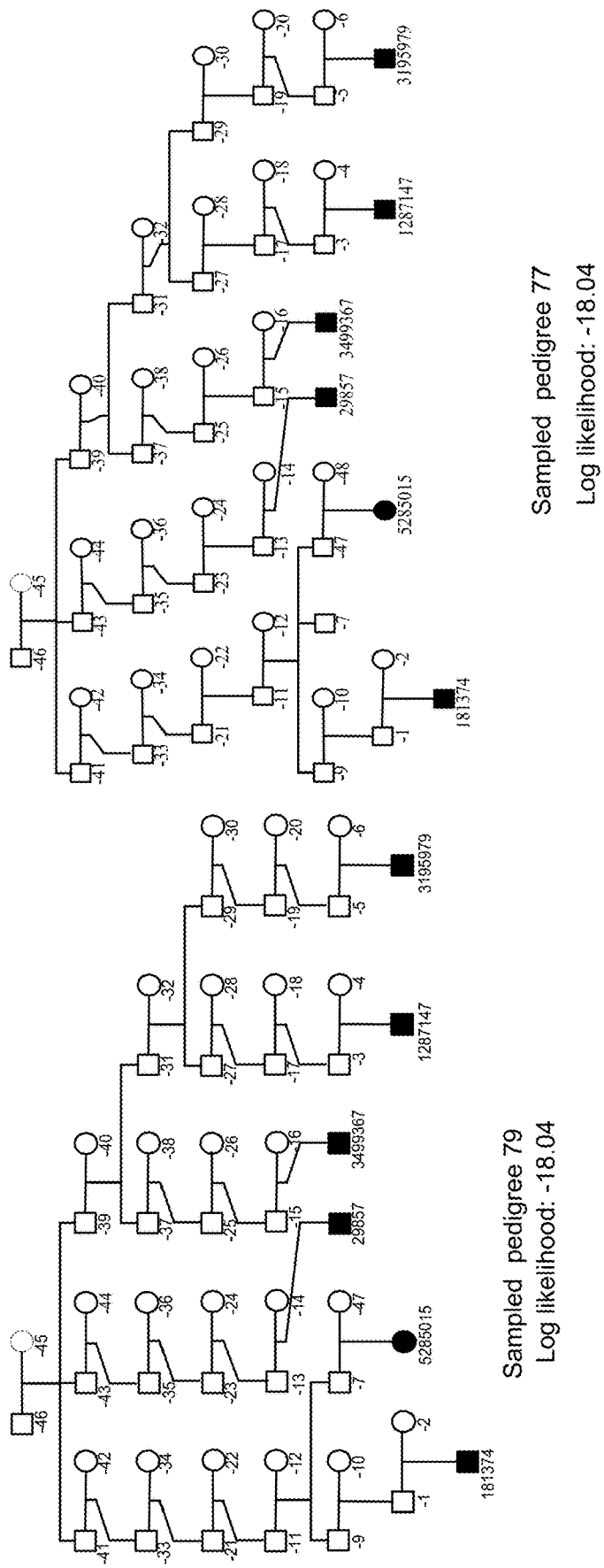

To illustrate with a dataset, a simulated dataset with ground truth is used to compare true family tree and estimated family tree with a top-ranking composite likelihood score. First, a group of family trees with different sizes and topology are sampled from the large-scale database "big tree" and genetic information for each family tree is simulated. Information with regard to which individuals have genetic information is included in the family tree. Then, sample one individual in the family tree that has genetic information as the target individual and mask the individual off in the individual's respective family tree. A simulation run is conducted with the ideal outcome to be matching the target individual back to the family tree that the individual originally belongs to. FIG. 14A illustrates one example of the true family tree that a target individual belongs to and FIG. 14B illustrates the two family trees with top log likelihood identified by the method.

Figure 15:
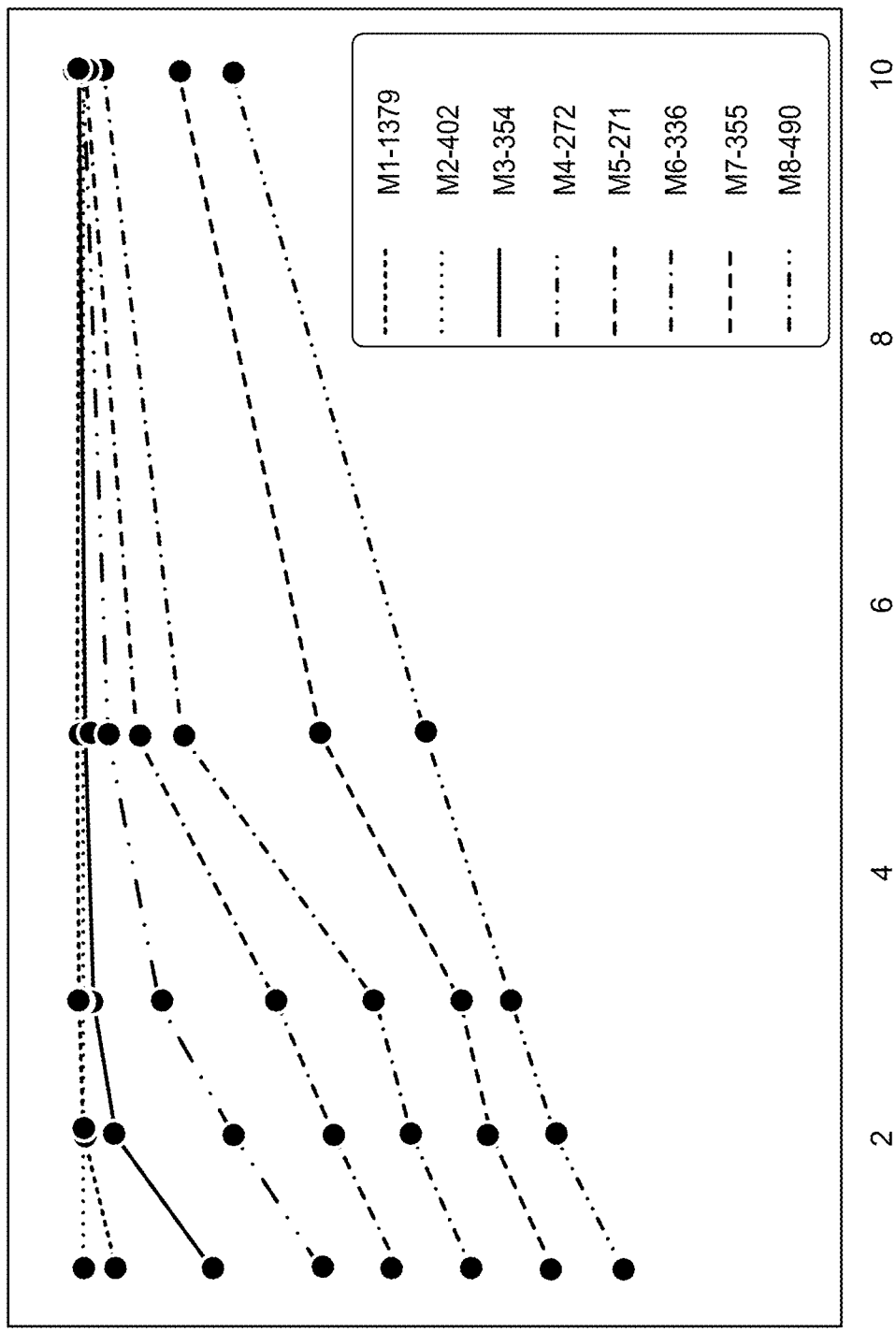
FIG. 15 illustrates the performance for each group of test family trees.

During the simulation, the test family trees are grouped into eight groups based on the relationship between the target individual and the individual's closest match in the family tree. Assume Mn is used to denote the relationship where Mn stands for meiosis level. For example, M1 means that the target individual has at least one match in the family tree that is one generation away. Intuitively, it is easier to estimate a position to place the target individual in the family tree if the meiosis level is low. FIG. 15 illustrates the performance for each group of test family trees. For M2 cases, the prediction accuracy may reach 150% accuracy with the family tree with the greatest composite likelihood. For M1 cases, the prediction accuracy may reach 150% with the top 2 ranked family trees. When false paternity cases are tested with simulated data (i.e. the target person does not belong to any given family tree), the chances to detect false paternity is 150%. FIG. 15 illustrates the results associated with different relationships where x axis indicates that the respective top x identified family trees and y axis indicates the percentage of test cases that have the true family tree among top x estimated family trees.

As such, the disclosed system identifies one or more family trees for the target individual and identifies a position in the family trees such that relationships between the target individual and individuals in the data tree are also determined. The disclosed system provides a solution to a challenging problem for existing implementation which is identification of family tree for a target individual who does not have available family tree information. The disclosed system is able to identify the most likely potential family trees with desirable results for a target individual based on genetic information and available information in the database. Furthermore, the disclosed system improves efficiency because of optimization steps such as pruning, ranking, and filtering based on meiosis and generation value information. These steps further filter information that is likely to be not useful and therefore reduces computational complexity.

CALCULATING M

The evaluation of evidence depends on how m, the tree relationship, is calculated. For a simple case, which is a full relationship with only one pair of observed common ancestors, m is the number of hops between the two individuals (e.g., 1st cousins are m4).

More complicated relationships can be fit into the framework below. (1) For any half relationship between two individuals, use the m(x+1) distribution. (2) Inbreeding adds another path to the common ancestor couple. This acts the same as if there was a completely different ancestor. For example, m8wm6mg (m8 relationship with an m6 marriage in one of the lines) is the same as m8+m8. If the cousin marriage happens on a path that is longer than the closest path, then that is reflected accordingly (i.e. m8+m9). (3) 2m(x) is equal to m(x−1). That is, m8+m8=m7. (4) m(x)+m(x+1) is equal to a distribution halfway between the m(x) and m(x−1) distributions. In this case, the higher score between the distributions should be used. (5) m(x)+m(x+y) where y>1 is very close to the m(x) distribution. This distribution or the max between the m(x) and m(x−1) distributions could be used.

For example, consider the following relationship:

$$m7+m8+m8wm7mg+m9+m9wm6mg+m10+m10+m11$$

The above relationship can be simplified by first expanding the marriage inbreeding relationships:

$$m7+m8+m8+m9+m9+m9+m9+m10+m10+m11$$

The relationship can be further simplified by considering the combinations of relationships, highest relationships first:

$$m7+m8+m8+m9+m9+m9+m9+m9+m11$$

$$m7+m8+m8+m8+m9+m9+m9+m11$$

$$m7+m8+m8+m8+m8+m9+m11$$

$$m7+m7+m8+m8+m9+m11$$

$$m7+m7+m7+m9+m11$$

$$m6+m7+m9+m11$$

The relationship distribution is expected to be between the m6 and m7 distributions. The computing server 130 may run both m6 and m7 and take the maximum score.

COMPUTING MACHINE ARCHITECTURE

Figure 16:
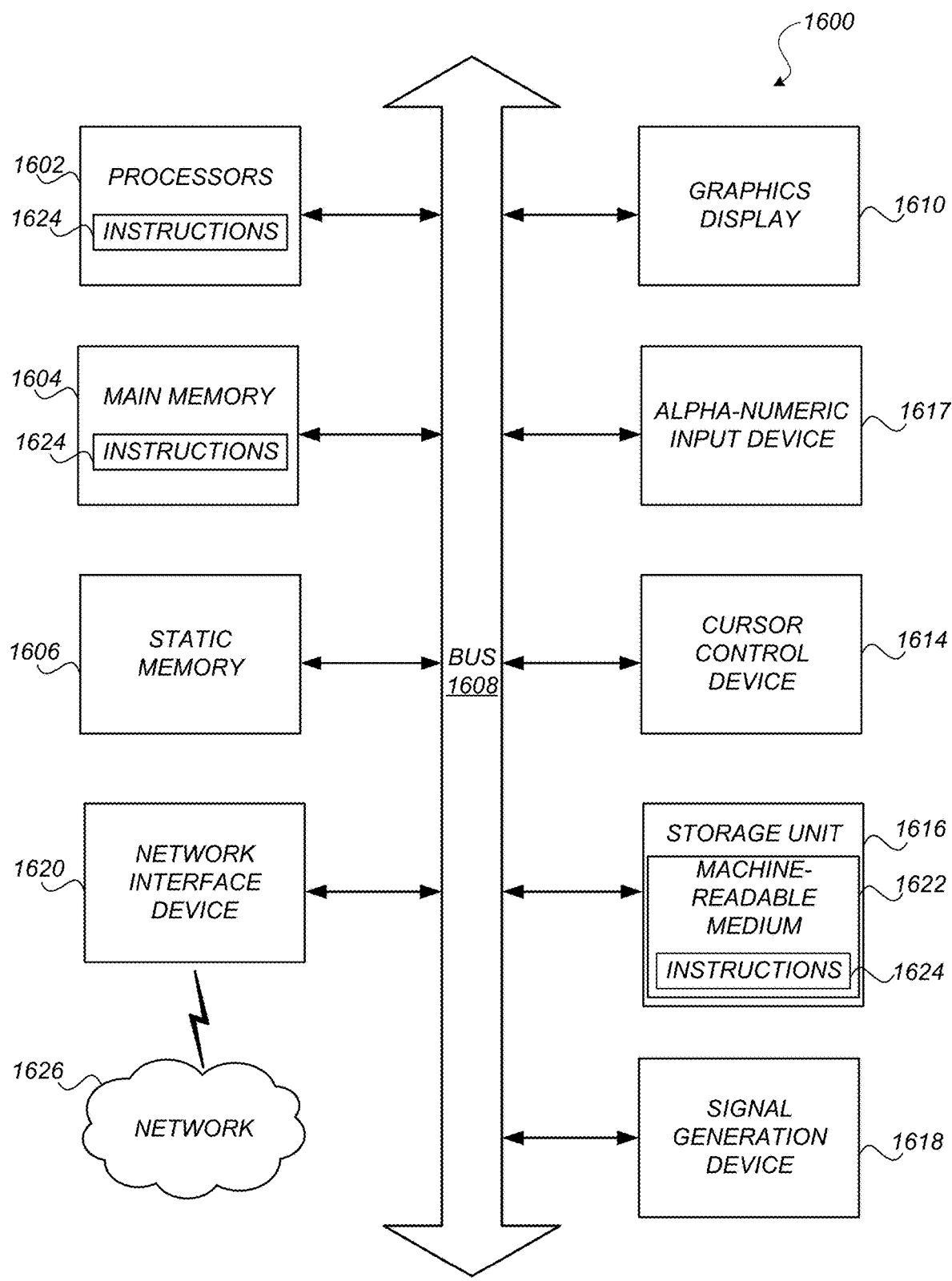
FIG. 16 is a block diagram illustrating components of an example computing machine that is capable of reading instructions.

FIG. 16 is a block diagram illustrating components of an example computing machine that is capable of reading instructions from a computer-readable medium and execute them in a processor (or controller). A computer described herein may include a single computing machine shown in FIG. 16, a virtual machine, a distributed computing system that includes multiples nodes of computing machines shown in FIG. 16, or any other suitable arrangement of computing devices.

By way of example, FIG. 16 shows a diagrammatic representation of a computing machine in the example form of a computer system 1600 within which instructions 1624 (e.g., software, source code, program code, expanded code, object code, assembly code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 16 may correspond to any software, hardware, or combined components shown in FIGS. 1 and 2, including but not limited to, the client device 110, the computing server 130, and various engines, interfaces, terminals, and machines shown in FIG. 2. While FIG. 16 shows various hardware and software elements, each of the components described in FIGS. 1 and 2 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1624 that specify actions to be taken by that machine. Further, while only a single machine is illustrated, the term "machine" and "computer" may also be taken to include any collection of machines that individually or jointly execute instructions 1624 to perform any one or more of the methodologies discussed herein.

The example computer system 1600 includes one or more processors 1602 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 1600 may also include a memory 1604 that store computer code including instructions 1624 that may cause the processors 1602 to perform certain actions when the instructions are executed, directly or indirectly by the processors 1602. Instructions can be any directions, commands, or orders that may be stored in different forms, such as equipment-readable instructions, programming instructions including source code, and other communication signals and orders. Instructions may be used in a general sense and are not limited to machine-readable codes. One or more steps in various processes described may be performed by passing through instructions to one or more multiply-accumulate (MAC) units of the processors.

One and more methods described herein improve the operation speed of the processors 1602 and reduces the space required for the memory 1604. For example, the database processing techniques and machine learning methods described herein reduce the complexity of the computation of the processors 1602 by applying one or more novel techniques that simplify the steps in training, reaching convergence, and generating results of the processors 1602. The algorithms described herein also reduces the size of the models and datasets to reduce the storage space requirement for memory 1604.

The performance of certain of the operations may be distributed among the more than processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Even though in the specification or the claims may refer some processes to be performed by a processor, this should be construed to include a joint operation of multiple distributed processors.

The computer system 1600 may include a main memory 1604, and a static memory 1606, which are configured to communicate with each other via a bus 1608. The computer system 1600 may further include a graphics display unit 1610 (e.g., a plasma display panel (PDP), a liquid crystal display (LCD), a projector, or a cathode ray tube (CRT)). The graphics display unit 1610, controlled by the processors 1602, displays a graphical user interface (GUI) to display one or more results and data generated by the processes described herein. The computer system 1600 may also include alphanumeric input device 1612 (e.g., a keyboard), a cursor control device 1614 (e.g., a mouse, a trackball, a joystick, a motion sensor, or other pointing instrument), a storage unit 1616 (a hard drive, a solid state drive, a hybrid drive, a memory disk, etc.), a signal generation device 1618 (e.g., a speaker), and a network interface device 1620, which also are configured to communicate via the bus 1608.

The storage unit 1616 includes a computer-readable medium 1622 on which is stored instructions 1624 embodying any one or more of the methodologies or functions described herein. The instructions 1624 may also reside, completely or at least partially, within the main memory 1604 or within the processor 1602 (e.g., within a processor's cache memory) during execution thereof by the computer system 1600, the main memory 1604 and the processor 1602 also constituting computer-readable media. The instructions 1624 may be transmitted or received over a network 1626 via the network interface device 1620.

While computer-readable medium 1622 is shown in an example embodiment to be a single medium, the term "computer-readable medium" should be taken to include a single medium or multiple media (e.g., a centralized or distributed database, or associated caches and servers) able to store instructions (e.g., instructions 1624). The computer-readable medium may include any medium that is capable of storing instructions (e.g., instructions 1624) for execution by the processors (e.g., processors 1602) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

ADDITIONAL CONSIDERATIONS

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The following applications are incorporated by reference in their entirety for all purposes: (1) U.S. Pat. No. 10,679,729, entitled "Haplotype Phasing Models," granted on Jun. 9, 2020, (2) U.S. Pat. No. 10,223,498, entitled "Discovering Population Structure from Patterns of Identity-By-Descent," granted on Mar. 5, 2019, (3) U.S. Pat. No. 10,720,229, entitled "Reducing Error in Predicted Genetic Relationships," granted on Jul. 21, 2020, (4) U.S. Pat. No. 10,558,930, entitled "Local Genetic Ethnicity Determination System," granted on Feb. 11, 2020, and (5) U.S. Pat. No. 10,114,922, entitled "Identifying Ancestral Relationships Using a Continuous Stream of Input," granted on Oct. 30, 2018.

What is claimed is:

1. A computer-implemented method, comprising:
    receiving a target individual genetic dataset associated with a target individual;
    identifying a plurality of matched individuals who genetically match with the target individual;
    identifying a plurality of potential ancestors who are potential common ancestors between the target individual and one of the matched individuals;
    inputting a set of features related to the target individual to a machine learning model, wherein training of the machine learning model comprises:
        generating a plurality of training samples, wherein generating one of the plurality of training samples comprises:
            identifying a training target individual, the training target individual having a genetic dataset,
            identifying ancestors of the training target individual from one or more family trees of the training target individual,
            determining, based on existing family trees that includes the training target individuals, whether each of the ancestors is a direct-line ancestor of the training target individual, and
            assigning a positive label to a particular ancestor responsive to the particular ancestor being a direct-line ancestor of the training target individual; and
        training the machine learning model using the plurality of training samples;
    filtering the plurality of potential common ancestors using the machine learning model to identify a subset of the potential common ancestors of the target individual.

2. The computer-implemented method of claim 1, wherein the target individual and the plurality of matched individuals are related by identity by descent (IBD).

3. The computer-implemented method of claim 1, wherein a potential common ancestor of the plurality of potential common ancestors is documented in a family tree of one of the matched individuals.

4. The computer-implemented method of claim 1, wherein identifying a matched individual of the plurality of matched individuals comprises:
    receiving a candidate individual genetic dataset of a candidate individual;
    identifying matched genetic segments between the candidate individual genetic dataset and the target individual;
    measuring a total length of the matched genetic segments in centimorgans; and
    classifying the candidate individual as the matched individual responsive to the total length exceeding a threshold.

5. The computer-implemented method of claim 4, wherein the set of features includes the total length of the matched genetic segments in centimorgans.

6. The computer-implemented method of claim 1, wherein the set of features includes a generation difference between a potential common ancestor and a matched individual.

7. The computer-implemented method of claim 1, wherein the set of features includes an age difference between the target individual and a potential common ancestor.

8. The computer-implemented method of claim 1, wherein the set of features includes a percentage of descendants in a family tree of a potential common ancestor who are matched individuals of the target individual.

9. The computer-implemented method of claim 1, wherein the machine learning model is a supervised learning model.

10. The computer-implemented method of claim 1, wherein the potential common ancestors in the subset of the potential common ancestors are more likely to be direct-line ancestors of the target individual than other potential common ancestors that are filtered out by the machine learning model.

11. The computer-implemented method of claim 1, wherein the machine learning model is configured to provide at least a label that a potential common ancestor is a direct-line ancestor or not.

12. The computer-implemented method of claim 1, wherein training of the machine learning model comprises:
    generating a plurality of training samples, the plurality of training samples comprising a set of positive training samples and a set of negative training samples;
    extracting training features of the plurality of training samples to generate a plurality of feature vectors, each feature vector corresponding to one of the training samples;
    inputting the plurality of feature vectors to the machine learning model;
    using the machine learning model to predict labels of one or more ancestors in the training samples;
    determining an objective function that compares the predicted labels to actual labels of the training samples; and adjusting one or more weights of the machine learning model based on the objective function.

13. A non-transitory computer readable medium configured to store computer code comprising instructions, the instructions, when executed by one or more processors, cause the one or more processors to perform steps comprising:
   receiving a target individual genetic dataset associated with a target individual;
   identifying a plurality of matched individuals who genetically match with the target individual;
   identifying a plurality of potential ancestors who are potential common ancestors between the target individual and one of the matched individuals;
   inputting a set of features related to the target individual to a machine learning model, wherein training of the machine learning model comprises:
      generating a plurality of training samples, wherein generating one of the plurality of training samples comprises:
         identifying a training target individual, the training target individual having a genetic dataset,
         identifying ancestors of the training target individual from one or more family trees of the training target individual,
         determining, based on existing family trees that includes the training target individuals, whether each of the ancestors is a direct-line ancestor of the training target individual, and
         assigning a positive label to a particular ancestor responsive to the particular ancestor being a direct-line ancestor of the training target individual; and
      training the machine learning model using the plurality of training samples; and
   filtering the plurality of potential common ancestors using the machine learning model to identify a subset of the potential common ancestors of the target individual.

14. The non-transitory computer readable medium of claim 13, wherein a potential common ancestor of the plurality of potential common ancestors is documented in a family tree of one of the matched individuals.

15. The non-transitory computer readable medium of claim 13, wherein identifying a matched individual of the plurality of matched individuals comprises:
   receiving a candidate individual genetic dataset of a candidate individual;
   identifying matched genetic segments between the candidate individual genetic dataset and the target individual;
   measuring a total length of the matched genetic segments in centimorgans; and
   classifying the candidate individual as the matched individual responsive to the total length exceeding a threshold.

16. The non-transitory computer readable medium of claim 13, wherein the machine learning model is a supervised learning model.

17. The non-transitory computer readable medium of claim 13, wherein training of the machine learning model comprises:
   generating a plurality of training samples, the plurality of training samples comprising a set of positive training samples and a set of negative training samples;
   extracting training features of the plurality of training samples to generate a plurality of feature vectors, each feature vector corresponding to one of the training samples;
   inputting the plurality of feature vectors to the machine learning model;
   using the machine learning model to predict labels of one or more ancestors in the training samples;
   determining an objective function that compares the predicted labels to actual labels of the training samples; and
   adjusting one or more weights of the machine learning model based on the objective function.

18. A system comprising:
   one or more processors; and
   memory configured to store computer code comprising instructions, the instructions, when executed by one or more processors, cause the one or more processors to perform steps comprising:
      receiving a target individual genetic dataset associated with a target individual;
      identifying a plurality of matched individuals who genetically match with the target individual;
      identifying a plurality of potential ancestors who are potential common ancestors between the target individual and one of the matched individuals;
      inputting a set of features related to the target individual to a machine learning model, wherein training of the machine learning model comprises:
         generating a plurality of training samples, wherein generating one of the plurality of training samples comprises:
            identifying a training target individual, the training target individual having a genetic dataset,
            identifying ancestors of the training target individual from one or more family trees of the training target individual,
            determining, based on existing family trees that includes the training target individuals, whether each of the ancestors is a direct-line ancestor of the training target individual, and
            assigning a positive label to a particular ancestor responsive to the particular ancestor being a direct-line ancestor of the training target individual, and training the machine learning model using the plurality of training samples; and
      filtering the plurality of potential common ancestors using the machine learning model to identify a subset of the potential common ancestors of the target individual.

* * * * *